(12) United States Patent
Leu et al.

(10) Patent No.: US 8,298,526 B2
(45) Date of Patent: *Oct. 30, 2012

(54) LACTOBACILLUS STRAIN, COMPOSITION AND USE THEREOF FOR IMPROVING THE SYNDROME OF DIABETES AND COMPLICATION THEREOF

(75) Inventors: Ying-Chen Leu, Tainan County (TW); Feng-Ching Hsieh, Tainan County (TW)

(73) Assignee: Genmont Biotech Inc., Tainan County (TW)

(*) Notice: Subject to any disclaimer, the term of this patent is extended or adjusted under 35 U.S.C. 154(b) by 208 days.

This patent is subject to a terminal disclaimer.

(21) Appl. No.: 12/792,276

(22) Filed: Jun. 2, 2010

(65) Prior Publication Data

US 2011/0300117 A1 Dec. 8, 2011

(51) Int. Cl.
*A01N 63/00* (2006.01)
*A01N 65/00* (2009.01)

(52) U.S. Cl. .................................. 424/93.1; 424/93.45

(58) Field of Classification Search .................. None
See application file for complete search history.

(56) References Cited

U.S. PATENT DOCUMENTS 7,901,926 B2* 3/2011 Yu et al. ............. 435/252.9

* cited by examiner

*Primary Examiner* — Albert Navarro
(74) *Attorney, Agent, or Firm* — WPAT, P.C.; Anthony King

(57) ABSTRACT

The invention relates to a composition for improving the syndrome of diabetes and complication thereof. The composition comprises an effective amount of *Lactobacillus* strain which is at least one selected from the group consisting of: *Lactobacillus reuteri* GMNL-89 strain, *Lactobacillus gasseri* GMNL-205 strain, *Lactobacillus reuteri* GMNL-263 strain and a pharmaceutical acceptable vehicle. The *Lactobacillus gasseri* GMNL-205 strain and *Lactobacillus reuteri* GMNL-263 strain are novel isolated *Lactobacillus* strains. In addition, the invention also relates to a novel use of the composition or the *Lactobacillus* strains for improving the syndrome of diabetes and complication thereof.

5 Claims, 16 Drawing Sheets

SEQUENCE LISTING

<160> NUMBER OF SEQ ID NOS: 3

<210> SEQ ID NO 1
<211> LENGTH: 506
<212> TYPE: DNA
<213> ORGANISM: Lactobacillus gasseri GMNL-205 strain
<220> FEATURE:
<223> OTHER INFORMATION:

<400> SEQUENCE: 1

| gacgaacgct | ggcggcgtgc | ctaatacatg | caagtcgagc | gagcttgcct | agatgaattt | 60 |
| ggtgcttgca | ccaaatgaaa | ctagatacaa | gcgagcggcg | gacgggtgag | taacacgtgg | 120 |
| gtaacctgcc | caagagactg | ggataacacc | tggaaacaga | tgctaatacc | ggataacaac | 180 |
| actagacgca | tgtctagagt | ttaaaagatg | gttctgctat | cactcttgga | tggacctgcg | 240 |
| gtgcattagc | tagttggtaa | ggtaacggct | taccaaggca | atgatgcata | gccgagttga | 300 |
| gagactgatc | ggccacattg | ggactgagac | acggcccaaa | ctcctacggg | aggcagcagt | 360 |
| agggaatctt | ccacaatgga | cgcaagtctg | atggagcaac | gccgcgtgag | tgaagaaggg | 420 |
| tttcggctcg | taaagctctg | ttggtagtga | agaaagatag | aggtagtaac | tggccttat | 480 |
| ttgacggtaa | ttacttagaa | agtcac | | | | 506 |

<210> SEQ ID NO 2
<211> LENGTH: 560
<212> TYPE: DNA
<213> ORGANISM: Lactobacillus reuteri GMNL-263 strain
<220> FEATURE:
<223> OTHER INFORMATION:

<400> SEQUENCE: 2

| gatgaacgcc | ggcggtgtgc | ctaatacatg | caagtcgtac | gcactggccc | aactgattga | 60 |
| tggtgcttgc | acctgattga | cgatggatca | ccagtgagtg | gcggacgggt | gagtaacacg | 120 |
| taggtaacct | gccccggagc | ggggggataac | atttggaaac | agatgctaat | accgcataac | 180 |
| aacaaaagcc | acatggcttt | tgtttgaaag | atggctttgg | ctatcactct | gggatggacc | 240 |
| tgcggtgcat | tagctagttg | gtaaggtaac | ggcttaccaa | ggcgatgatg | catagccgag | 300 |
| ttgagagact | gatcggccac | aatggaactg | agacacggtc | catactccta | cgggaggcag | 360 |
| cagtagggaa | tcttccacaa | tgggcgcaag | cctgatggag | caacaccgcg | tgagtgaaga | 420 |
| agggtttcgg | ctcgtaaagc | tctgttgttg | gagaagaacg | tgcgtgagag | taactgttca | 480 |
| cgcagtgacg | gtatccaacc | agaaagtcac | ggctaactac | gtgccagcag | ccgcggtaat | 540 |
| acgtaggtgg | caagcgttat | | | | | 560 |

<210> SEQ ID NO 3
<211> LENGTH: 10
<212> TYPE: DNA
<213> ORGANISM: artificial sequence
<220> FEATURE:
<223> OTHER INFORMATION: primer for RAPD analysis

<400> SEQUENCE: 3

| atgtaacgcc | | | | | | 10 |

LACTOBACILLUS STRAIN, COMPOSITION AND USE THEREOF FOR IMPROVING THE SYNDROME OF DIABETES AND COMPLICATION THEREOF

BACKGROUND OF THE INVENTION

1. Field of the Invention

The invention relates to technical field of isolation of novel *Lactobacillus* isolated, and its use for improving the syndrome of diabetes and complication thereof.

2. Description of the Prior Art

Diabetes Mellitus is a metabolism disease of many pathogens. It is a disease caused by extensive metabolism dysfunction that is induced due to the defect produced in the secretion or action of insulin. Main feature of diabetes consists of constant chronic high blood sugar, as well as metabolic disorder of protein, lipid, water, electrolyte and the like.

Clinically, diabetes is classified mainly into two types:

Type 1: Insulin-dependent diabetic mellitus (IDDM), occurs mostly in the ages less than 30 years, and as such has been named as "Juvenile—Onset diabetes", but actually it may occur in any age. Type 1 diabetes is an autoimmune disease in which the immunological system itself attacks β cell of islet of Langerhans in pancreas. Its cause involves personal genetics, virus infection, or damage of toxic substance on β cell of pancreas, antibody against β cell formed by autoimmunology, and attacking on β cell by cell immunological action. Eventually, pancreas of the subject cannot secret insulin normally, becomes extremely susceptible to toketoacidosis, and needs insulin injection for treating.

Type 2: Non-insulin dependent diabetic mellitus (NIDDM), occurs mostly in the age after 40 years. Most subjects of this type are fat, and therefore, this type has been called "maturity onset diabetes" in the past, but may occur on young men, and is often seen in familial occurrence. This type of diabetes consists of more than 95% of total diabetes population in Taiwan. This type of diabetes is caused by the defect of insulin secretion, and insulin resistance; in which, though insulin secretion of part of subjects may be decreased, most subjects have acceptable ability to secret insulin. Therefore, its treatment depends largely on dietary control and oral administration of blood sugar-lowering drug to control blood sugar, and need not inject insulin instantly. In addition, most subjects may be accompanied with insulin resistance. Formation of insulin resistance comes primarily from the excess secretion of insulin (hyperinsulinamia) by the β cell of islet of Langerhans in pancreas, which causes the lowering of insulin sensitivity of peripheral tissues such as skeleton muscles, fat tissues, liver and the like, thereby diminishing the utilization of glucose in these tissues, and hence inducing the phenomenon of high blood sugar. Progression of this type is slow, no typical diabetes symptom emerges in early stage and hence is not easy to detect. It is accompanied usually with chronic complications such as diabetic pathogenic change of large vessel (for example, cardiomuscular infarction, and brain stroke), small vessel (for example in kidney, retina and nerve) and the like.

In addition, subjects of type 2 diabetes are accompanied usually with abnormal lipid metabolic conditions, such as increasing of triglyceride (TG) concentration, lowering of high density lipoprotein cholesterol (HDL-C) concentration and increasing of low density lipoprotein cholesterol (LDL-C) concentration in the plasma. This syndrome may incur in type 2 diabetes subjects with risk of cardiovascular diseases. Further, it has been pointed out that serious diabetes subjects might diminish their ability to clear blood lipid in liver. When triglyceride and low density lipoprotein cholesterol have been accumulated continuously to some extent, pathological change of liver cell may occur to form non-alcoholic fatty liver and affect liver function severely.

Other than administration of insulin, two additional ways for treating diabetes consists of non-drug and drug treatments. Non-drug treatment resides mainly on dietary regulation and sport. Whereas in the aspect of drug treatment, its primary object involves rising the deficiency of insulin, regulating down the high blood sugar after meal, improving insulin resistance and the like. At present, drugs used to treat diabetes may include:

(1) Sulfonylurea: The main mechanism of this type of drug is to promote the secretion of insulin from pancreas, especially to enhance the stimulation of pancreatic β cell against glucose so as to release insulin; commonly used sulfonylurea blood sugar-lowering drug includes glibenclamide (trade name: Euglucon), glipizide (trade name: Minidiab) and gliclazide (trade name: Diamicron). However, in addition to its side-effect, such as rash, and pruritus, its application to subjects is also limited. For example, one that has severe liver, and kidney dysfunction, pregnant women and nurses, and one that has severe sensitivity to sulfonylurea drug, are all not suitable to use this type of blood sugar-lowering drug.

(2) α-Glucosidase inhibitor: The main mechanism of this type of drug is to inhibit activities of pancreatic α-amylase and intra-intestinal α-glucosidase, and further inhibit the decomposition and absorption of carbohydrate in the intestinal tract. This type of drug can lower effectively the blood sugar after meal and insulin concentration, with side-effect of abdominal distention or occasional diarrhea, bellyache and nausea.

(3) Thiazolidinedione derivatives: The main action of this type of drug is to increase the activity of peroxisome proliferator-activated receptor (PPAR)-gamma in the cell nucleus, and further enhance the effect of insulin, such that glucose transfer protein GLUT2 and GLUT4 in the cell is increased so as to transport glucose into the cell for use. Commonly used one in clinic includes troglitazone (trade name: Rezulin), rosiglitazone (trade name: Avandia), pioglitazone (trade name: Actos) and the like. Among these, troglitazone had induced lethal liver-toxicity, and therefore, it had been prohibited to be used two months after marketing in England (October, 1997). Furthermore, thiazolidinedione derivatives had been suffered by the USA to issue an order to withdraw comprehensively and to be forbidden to use.

(4) Biguanides: This type of drug belongs to guanidine derivative. At present, biguanide blood sugar-lowering drug now is mainly metformin. This type of drug does not itself stimulate the secretion of insulin. Main mechanism in controlling blood sugar consists of following five points: a Inhibiting appetite, and therefore is used preferably for fat type 2 diabetes subjects to reduce their appetites, lower their body weight and further improve the peripheral action of insulin; b. Retarding the absorption of glucose by the intestinal tract; c. Promoting the anaerobic decomposition of glucose in the intestinal tract, and further increase the utilization of glucose in the intestinal tract, however, this may produce excess lactate that is susceptible to cause lactic acidosis; d. Enhancing the action of insulin in the liver, thereby inhibiting the neogenesis of glucose in liver, and reduce the release of glucose from liver; e. Promoting glucose transfer protein GLUT4 stored in the cell to move to the cell surface and to participate in the action of glucose transport, thereby increasing significantly the amount of glucose transfer protein on the cell surface. This type of blood sugar-lowering drug has some side-effects such as gastrointestinal discomfort in the first administration, for example anorexia, nausea, omitting, diarrhea and the like, few ones may present possibly skin rash, and after long-term use, will occur inactivation phenomenon.

*Lactobacillus* has extensive uses, which include, other than the preparation of fermented foods, many good functions, such as: 1. Secreting various decomposing enzymes to help decomposition of foods, and thus increasing nutritional value; 2. Decomposing lactose to improve lactose intolerance; 3. Secreting vitamin B group; 4. Maintaining normal microbial flora in the intestinal tract and suppressing the action of harmful bacteria; 5. Ameliorating diarrhea or constipation, 6. Strengthening functions of immunological system; 7. Improving liver function and diminishing the damage on liver; 8. Lowering blood cholesterol; 9. anti-cancer and anti-mutagenesis. In addition, it had been found that feeding rat with *Lactobacillus* could retard the occurrence of diabetes. Several literatures or patent had pointed out that feeding rats with *Lactobacillus* could prevent diabetes effectively and lower the concentration of blood sugar. However, contents of literatures or patents associated with the improvement effect of *Lactobacillus* on diabetes published up to now were limited to just control blood sugar value, body weight, and concentrations of lipid and cholesterol in blood. None of these disclosed about the effect of improving other complication that might be induced by diabetes, such as inflammation reaction in the body and decay of liver function. In addition to blood sugar value, blood lipid and cholesterol, improvement on blood glycated hemoglobin, inflammation cytokine and liver lipid as well as liver function index GOT and GPT need further study.

Drugs for treating diabetes clinically all have a lot of side-effects. On the contrary, *Lactobacillus* is a probiotics Generally Recognized As Safe (GRAS). Therefore, it is a natural and healthy way to develop a product for improving diabetes by using *Lactobacillus*.

In view of the above-described side-effects and limits in use of present diabetes drugs, and the considerations that treatment of diabetes need the cooperation of, as well as diabetes being a chronic disease needing long-term treatment and control, the inventor was devoted to improve and innovate in order to develop a product for improving diabetes syndrome by using *Lactobacillus* strain such that the product can be used by ordinary users or diabetes subjects in daily life to improve, control, treat or prevent diabetes syndrome such as high blood sugar, high cholesterol and the like and possible complication, and finally, after studying intensively for many years, developed successfully the inventive novel *Lactobacillus*, composition containing the same, and method for improving diabetes and complication thereof.

SUMMARY OF THE INVENTION

One object of the invention is to provide a composition for improving syndrome of diabetes and complication thereof, comprising an effective amount *Lactobacillus* bacteria which is at least one selected from the group consisting of *Lactobacillus reuteri* GMNL-89, *Lactobacillus gasseri* GMNL-205 and *Lactobacillus reuteri* GMNL-263, and a pharmaceutically acceptable vehicle.

Another object of the invention is to provide a novel *Lactobacillus* isolated strain, *Lactobacillus gasseri* GMNL-205.

Another object of the invention is to provide a novel *Lactobacillus* isolated strain, *Lactobacillus reuteri* GMNL-263.

Another object of the invention is to provide a novel use of a known *Lactobacillus* isolated strain, and two novel *Lactobacillus* isolated strain, said isolated strains can be used by diabetes subject for improving the syndrome of diabetes and complication thereof.

Yet still another object of the invention is to provide a method for improving the syndrome of diabetes and complication thereof, comprising of administering either one of these two novel *Lactobacillus* strains or compositions containing the same to the diabetes subjects.

Yet still another object of the invention is to provide an application of either one of these two novel *Lactobacillus* strains or compositions containing the same for improving the syndrome of diabetes and complication thereof, in forms of food, beverage, health foods, additives, pharmaceutical compositions and the like, to be easily and long-term administrated by normal people or chronic diabetes subjects to achieve the purpose of health care or disease control.

The novel *Lactobacillus* strains, composition containing the same, and their use for improving the syndrome of diabetes and complication thereof that can achieve the above-described objects of the invention include a *Lactobacillus reuteri* GMNL-89 with deposition number: CCTCC M207154; a *Lactobacillus gasseri* GMNL-205 with deposition number: CCTCC M209262; and a *Lactobacillus reuteri* GMNL-263 with deposition number: CCTCC M209263. New deposits have been made to CCTCC (China Center for Type Culture Collection) located at Wuhan University, Wuhan 430072 P.R. China, which belongs to International Depository Authority (IDA) under the Budapest Treaty. The deposit of CCTCC M207154 was received on Nov. 19, 2007, the deposit of CCTCC M209262 was received on Nov. 13, 2007, and the deposit of CCTCC M209263 was received on Nov. 13, 2007. The viability of the above mentioned cultures were tested on Nov. 26, 2007 and were tested to be viable.

These two novel *Lactobacillus* isolated strains and a known *Lactobacillus reuteri* GMNL-89 strain (deposited with deposition number of CCTCC M207154) are subjected to diabetes animal model analysis to evaluate whether said Lactobacillus isolated strains have the effect of improving syndrome of diabetes and complication. Results indicate that those three *Lactobacillus* isolated strains can improve diabetes subject's syndrome such as high blood sugar value, high blood sugar value change, high glycated hemoglobin ratio, high total cholesterol concentration, high LDL/HDL ratio, high IFN-y level, high liver triglyceride lipid concentration, high liver cholesterol concentration and the like, and improve further diabetes and associated complications.

These features and advantages of the present invention will be fully understood and appreciated from the following detailed description of the accompanying Drawings.

DETAILED DESCRIPTION OF THE PREFERRED EMBODIMENT

Figure 1:
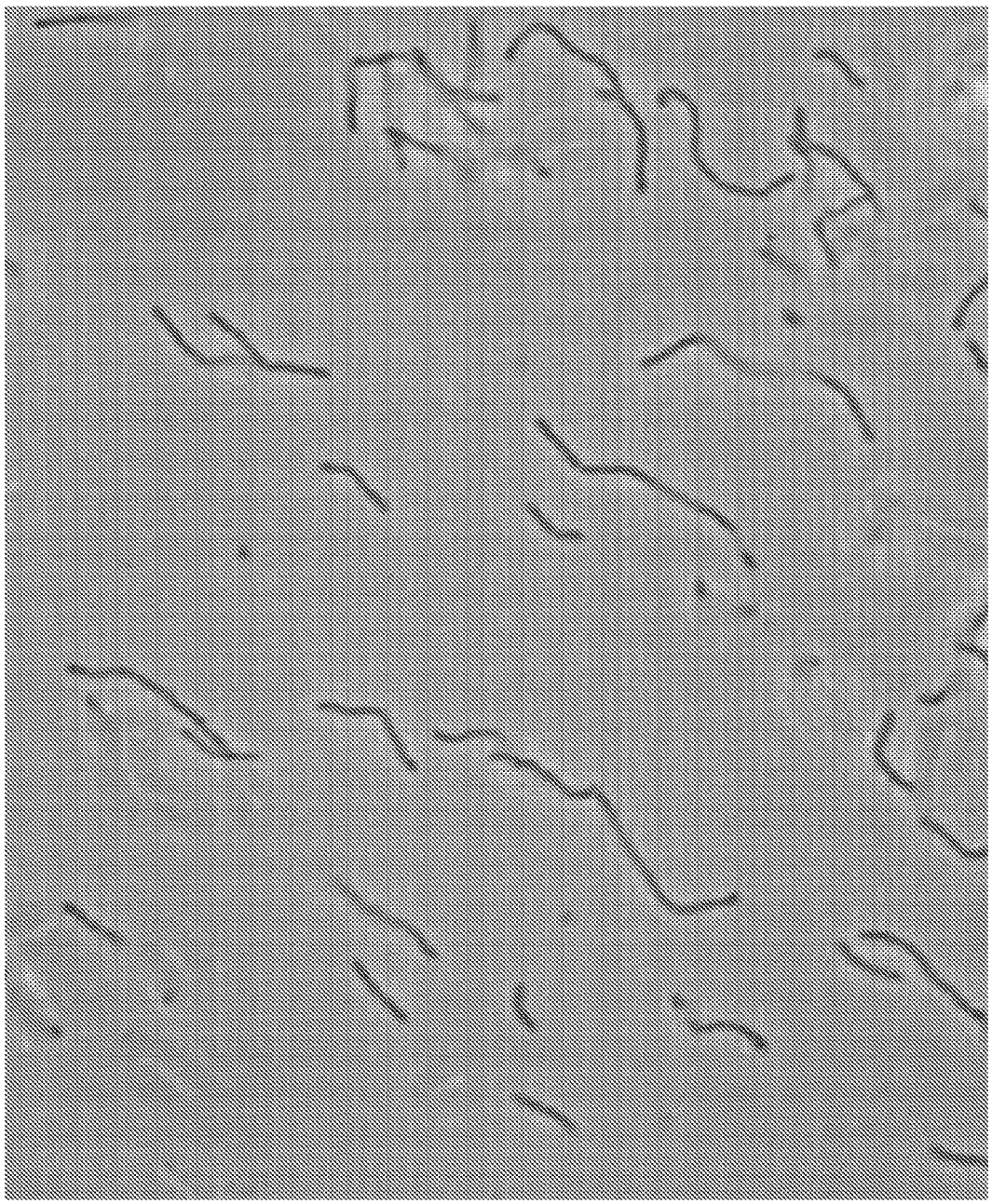
FIG. 1 is the morphology of *Lactobacillus gasseri* GMNL-205 under microscope.

Technical and scientific terms used in this specification, unless defined alternatively, otherwise have meanings commonly understood by the one ordinarily skilled in this technical field.

In one aspect, the invention provides a composition, comprising an effective amount of *Lactobacillus* bacteria which is at least one selected from the group consisting of: *Lactobacillus reuteri* GMNL-89 strain, *Lactobacillus gasseri* GMNL-205 strain, and *Lactobacillus reuteri* GMNL-263 strain, and a pharmaceutically acceptable vehicle.

Among those *Lactobacillus* bacteria strains in the composition, said *Lactobacillus reuteri* GMNL-89 is a known strain that had been disclosed in ROC Patent Application Pub. No.: 200944215, *"Lactobacillus* isolated strain with anti-inflammation activity and use thereof". Through diabetes animal model analysis, the applicant of this invention found that, in addition to its anti-inflammation activity, this strain has also function of improving diabetes syndrome.

In another aspect, the invention provides novel *Lactobacillus* strains, which are isolated from gastrointestinal specimens of healthy adults provided by hospitals, and include *Lactobacillus gasseri* GMNL-205, and *Lactobacillus reuteri* GMNL-263. These two strains had been subjected to bacteriological identification and gene map analysis and been confirmed as novel *Lactobacillus* isolated strains.

Those above-described three *Lactobacillus* isolated strains have been found through diabetes animal model analysis to improve, lower, control, treat and prevent effectively diabetes subject's high blood sugar value, high blood sugar value change, high glycated hemoglobin ratio, high total cholesterol concentration, high LDL/HDL ratio, high IFN-γ level, high liver triglyceride lipid concentration and high liver cholesterol concentration, and improve further the disease and associated complication.

Those *Lactobacillus* isolated strains comprise progeny or mutation strain thereof possessing same bacteriological characteristics, genome, or uses for improving diabetes syndrome as described in the invention.

"Composition" used herein refers to forms suitable to the application of the invention and may include, but not limited to, foods, beverages, health foods, additives in animal drinking water, animal feed additives, pharmaceutical compositions for animal and human being, food additives, beverage additives and the like.

Term "improving" means, compared with those that do not use *Lactobacillus* bacteria or composition containing the same, one that uses *Lactobacillus* bacteria or composition containing the same can retard, lower, control, treat or prevent effectively syndrome of diabetes and its associated complication.

Term "diabetes syndrome" includes, but not limited to: diabetes syndrome of diabetes subject expressed as high blood sugar value, high blood sugar value change, high glycated hemoglobin ratio, high total cholesterol concentration, high LDL/HDL ratio, high IFN-γ level, high liver triglyceride lipid concentration, high liver cholesterol concentration and the like.

Term "effective amount" means an amount of active ingredient that can improve, treat, diminish or eliminate one or more syndrome of a disease such as diabetes; it may be referred as "treating-effective" or "improving-effective".

Term "pharmaceutically acceptable" means substances to be used in the composition must be compatible with other components in the formulation and be harmless to the subject.

Term "diabetes associated complication" includes, but not limited to: diabetic nerve diseases (includes, but not limited to: adynamic bladder, abdominal distention, constipation, diarrhea, anaphrodisia, bad feeling to hot and cold), renal diseases (includes, but not limited to: glomerulonephritis, renal glomerulus scierosis, nephrotic syndrome, high blood pressure nephrosclerosis, last stage of kidney disease, uremia), inflammation reaction, cardiovascular or too high cholesterol complications (includes, but not limited to: brain stroke, cardiomuscular infarction, coronarothrombosis, sagina pectoris, heart failure, non-steady hear rhythm, bad end blood circulation, foot infection and the like), eye diseases (retina pathological change, cataract, glaucoma, amblyopia [weak sight]), liver diseases (includes, but not limited to: liver fibrosis, fatty liver, non-alcoholic fatty liver, and liver cirrhoris).

The inventive composition can be prepared into a dosage form suitable for the application of the inventive composition by using conventional technique well-known to one skilled in this art through formulating the above-described *Lactobacillus* isolated strain(s) with a pharmaceutically acceptable vehicle. The dosage form may include, but not limited to: solution, emulsion, suspension, powder, tablet, pill, lozenge, troche, chewing gum, capsule and other suitable forms.

Said pharmaceutically acceptable vehicles may include one or more agents selected from the following list: solvent, emulsifier, suspending agent, decomposer, binding agent, excipient, stabilizing agent, chelating agent, diluent, gelling agent, preservative, lubricant, surfactant, and other suitable vehicles.

In this composition, one or more dissolving aids, buffer, storage agent, colorant, fragrance, flavoring agent and the like commonly used in the above-described pharmaceutical field can be added as desired.

In one preferred embodiment, the inventive composition can be added further with an edible material to prepare food or health products. Said edible material may include, but not limited to: water, fluid milk products, milk, concentrated milk, fermented milk, yogurt, sour milk, frozen yogurt, lactic acid bacteria-fermented beverages, milk powder, ice cream, cream cheeses, dry cheeses, soybean milk, fermented soybean milk, vegetable-fruit juices, juices, sports drinks, confectionery, jelly, candies, infant formulas, health foods, animal feeds, Chinese herbals, dietary supplements, and the like.

Further, other than those novel strains, the inventive composition may comprise other conventional bacterial species. For example, the inventive composition may comprise further at least one probiotics selected from the group consisting of *Lactobacillus* sp., *Streptococcus* sp., *Bifidobacterium* sp., and yeasts.

Said conventional *Lactobacillus* sp. includes, but not limited to: *Lactobacillus lacti*), *Lactobacillus acidophilus*, *Lactobacillus helveticus*, *Lactobacillus bifidus*, *Lactobacillus casei*, *Lactobacillus paracasei* subsp. *paracasei*, *Lactobacillus rhamnosus*, *Lactobacillus gasseri*, *Lactobacillus reuteri*, *Lactobacillus fermentum*, or combination thereof.

Said conventional *Streptococcus* sp. includes, but not limited to: *Streptococcus lactis*, *Streptococcus thermophilus*, *Streptococcus cremoris*, or combination thereof.

Said conventional *Bifidobacterium* sp. includes, but not limited to: *Bifidobacterium breve*, *Bifidobacterium lactis*, *Bifidobacterium longum*, *Bifidobacterium bifidum*, or combination thereof.

Said conventional yeasts includes, but not limited to: *Saccharomyces cereviseae*, *Candida kefyr*, *Saccharomyces florentinus*, or combination thereof.

In still another aspect, the invention provides further a method for improving syndrome of diabetes and complications thereof, The method comprises of administrating an effective amount of the above-described composition to diabetes subject to improve and lower its high blood sugar value, blood sugar value change, glycated hemoglobin ratio, total cholesterol concentration, LDL/HDL ratio, IFN-γ level, high liver triglyceride lipid concentration, high liver cholesterol concentration, and liver function indexes GOT, and GPT, and further improve diabetes and associated complications.

Furthermore, the invention provides also a method and use of the above-described *Lactobacillus* in the preparation of the composition for improving syndrome of diabetes and its complication.

Delivery routes for the inventive composition and method can be adjusted as desired, and not been limited particularly. In an embodiment, oral dosage form is preferable.

The invention will be illustrated in more detail with following examples; however, the invention is not limited by these examples. Drugs and biological materials used in the invention are commercially available; those described in following examples are just exemplified available routes.

EXAMPLE 1

Strain Screening

Hundred of isolated strains were isolated from gastrointestinal specimens of healthy adults provided by hospital and thus established an isolated strain library. *Lactobacillus* strains that can regulate immune system to secrete high concentration of IL-10 and IFN-γ were selected from said library. *Lactobacillus* strains with first three analytical results were selected to be subjected to diabetes animal model analysis. Those three *Lactobacillus* strains have their deposition number (Access. No.), deposition date and strain name listed in Table 1. Among these, *Lactobacillus reuteri* GMNL-89 is a disclosed species with its strain characteristics, deposition certification, survivability test report and related information enclosed in ROC Patent application (application no.: 97115882; publication no.: 200944215). While *Lactobacillus* GMNL-205 and GMNL-263 are novel *Lactobacillus* strain isolated by the invention. Strain characteristics, API identification systematic analysis, 16S rDNA analysis, and gene chromatogram analysis of these two *Lactobacillus* strains will be described in the following Example 2 and 3.

TABLE 1

Deposition number (Dep. No.) and deposition date of the inventive *Lactobacillus* strains in the China Center For Type Culture Collection (CCTCC).

| Strain name | | Dep.. No. | Deposition date | |
|---|---|---|---|---|
| *Lactobacillus reuteri* | GMNL-89 | CCTCC M207154 | Nov. 14, 2006 | |
| *Lactobacillus gasseri* | GMNL-205 | CCTCC M209262 | Nov. 06, 2009 | App.1 |
| *Lactobacillus reuteri* | GMNL-263 | CCTCC M209263 | Nov. 06, 2009 | App.1 |

EXAMPLE 2

*Lactobacillus gasseri* GMNL-205

2-1. Scientific Name Identification of *Lactobacillus gasseri* GMNL-205 Strain

The isolated strain GMNL-205 was subjected to bacteriological scientific name identification in the Food Development and Research Institute as described hereinafter:

Background information of isolated strain GMNL-205:
1. Source: gastrointestinal tract of human body
2. Medium: MRS
3. Culturing temperature: 37° C.
4. Pathogenicity: no Referring to FIG. 1 and Table 2, analysis results indicated that isolated strain GMNL-205 was a Gram-positive bacillus without catalase, oxidase and mobility, and could be grown under both aerobic and anaerobic environments. Further, part 16S rDNA sequence of the isolated strain GMNL-205 is shown as in SEQ ID No: 1. In accordance with this 16S rDNA analysis, isolated strain GMNL-205 is more similar with *Lactobacillus gasseri*, *Lactobacillus taiwanensis* and *Lactobacillus johnsonii*, with an identity up to higher than 99%. Moreover, by means of API identification systematic analysis (Table 2), isolated strain GMNL-205 is closest to *Lactobacillus gasseri*. Therefore, according to the above-described results, isolated strain GMNL-205 is *Lactobacillus gasseri*.

TABLE 2

API identification analysis results of isolated strain GMNL-205.

| API Test | isolated strain GMNL-205 | *Lactobacillus gasseri* | *Lactobacillus taiwanensis* | *Lactobacillus johnsonii* |
|---|---|---|---|---|
| Glycerol | − | − | − | − |
| Erythritol | − | − | − | − |
| D-Arabinose | − | − | − | − |
| L-Arabinose | − | − | − | − |
| D-Ribose | − | − | − | − |

TABLE 2-continued

API identification analysis results of isolated strain GMNL-205.

| API Test | isolated strain GMNL-205 | Lactobacillus gasseri | Lactobacillus taiwanensis | Lactobacillus johnsonii |
|---|---|---|---|---|
| D-Xylose | − | − | − | − |
| L-Xylose | − | − | − | − |
| D-Adonitol | − | − | − | − |
| Methyl-βD-Xylopyranoside | − | − | − | − |
| D-Galactose | + | + | + | + |
| D-Glucose | + | + | + | + |
| D-Fructose | + | + | + | + |
| D-Mannose | + | + | + | + |
| L-Sorbose | − | − | − | − |
| L-Rhamnose | − | − | − | − |
| Dulcitol | − | − | − | − |
| Inositol | − | − | − | − |
| D-Mannitol | − | − | − | − |
| D-Sorbitol | − | − | − | − |
| Methyl-αD-mannopyranoside | − | − | − | − |
| Methyl-αD-glucopyranoside | − | − | − | − |
| N-AcetylGlucosamine | + | + | + | − |
| Amygdalin | − | + | − | − |
| Arbutin | + | + | − | − |
| Esculin | + | + | + | + |
| Salicin | + | + | − | − |
| D-Celiobiose | + | + | − | − |
| D-Maltose | + | + | + | + |
| D-Lactose | + | + | + | − |
| D-Melibiose | − | − | − | − |
| D-Saccharose | + | + | + | + |
| D-Trehalose | + | + | − | + |
| Inulin | − | − | − | − |
| D-Melezitose | − | − | − | − |
| D-Raffinose | − | − | + | − |
| Amidon | − | + | + | + |
| Glycogen | − | − | − | − |
| Xylitol | − | − | − | − |
| Gentiobiose | + | + | + | + |
| D-Turanose | − | − | − | − |
| D-Lyxose | − | − | − | − |
| D-Tagatose | − | + | + | − |
| D-Fucose | − | − | − | − |
| L-Fucose | − | − | − | − |
| D-Arabitol | − | − | − | − |
| L-Arabitol | − | − | − | − |
| Potassium Gluconate | − | − | − | − |
| Potassium 2-Ketogluconate | − | − | − | − |
| Potassium 5-Ketogluconate | − | − | − | − |
| 49 physiological and biochemical tests in total: Number of coincident items between isolated strain GMNL-205 and standard strain: | | 46 | 42 | 44 |

− Negative reaction;
+ Positive reaction 2-2. Gene Chromatogram Analysis of *Lactobacillus gasseri* GMNL-205 Strain Gene chromatogram of *Lactobacillus gasseri* GMNL-205 strain was analyzed by means of Random Amplified Polymorphic DNA (RAPD) analysis, in accordance with the experimental steps briefly described as followed.

A. Preparation of Strain Template:

GMNL-205 was inoculated on MRS medium, and cultured at 37° C. for 2 days. A single colony was selected from those on the MRS medium, inoculated under sterile condition in 1 ml MRS Broth, and was cultured at 37° C. for 16 hours. The liquor was centrifuged at 13000 rpm for 1 minute. The supernatant was discarded, and 200 µl sterile water was added to mix with the pellet homogeneously. The suspension was centrifuged at 13000 rpm for 1 minute, and discarded the supernatant. This step was repeated once more. To the thus washed pellet, 200 µl sterile water was added and mixed homogeneously, and this suspension was used to be the template in the RAPD experiment for the strain.

B. RAPD Analysis:

Primer Lac P2 (5'-ATg TAA CgC C-3', SEQ ID No: 3) was used in the PCR reaction. The composition of the PCR mixture was shown in Table 3:

TABLE 3

| Composition of PCR mixture | |
|---|---|
| Template | 1 µl |
| Lac P2 | 1 µl |
| dNTP mix | 1 µl |
| 10x Buffer | 2.5 µl |
| Ex Taq | 0.2 µl |
| H$_2$O | 19.3 µl |
| Total volume | 25 µl |

PCR reaction conditions: Reacting at first at 95° C. for 10 min, then 35 cycles of: denaturing reaction at 93° C. for 1 min, primer binding at 36° C. for 1 min, extending reaction at 72° C. for 1 min., and finally, reacting at 72° C. for 7 min, stopping PCR reaction, and stored at 4° C. After completion of PCR, 6 μl of PCR product was subjected to electrophoresis on 2% agarose gel, stained with EtBr, developed and photographed under UV lamp. The photograph was used to analyed as RAPD chromatogram of that single colony.

C. Experimental Results

Figure 2:
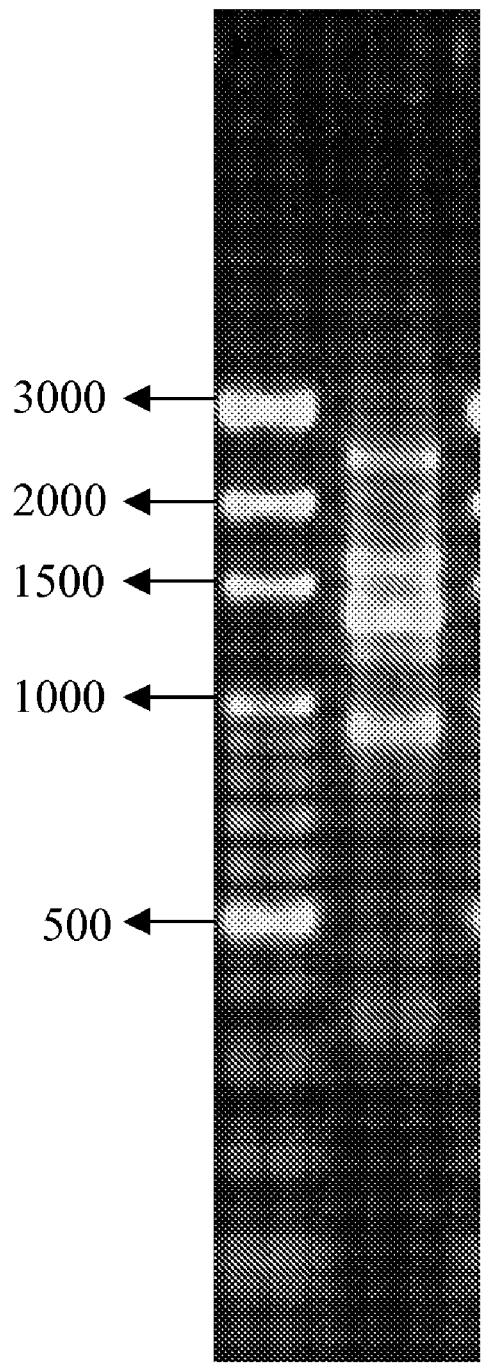
FIG. 2 is the gene chromatogram gene chromatogram of *Lactobacillus gasseri* GMNL-205; in which M represents molecular marker; and each arrow indicates molecular size (bp) of each fragment.

Referring to FIG. 2, gene chromatogram specifically possessed by GMNL-205 was clearly shown, which could used to recognize GMNL-205.

EXAMPLE 3

*Lactobacillus reuteri* GMNL-263

3-1. Scientific Name Identification of *Lactobacillus* GMNL-263 Strain

Figure 3:
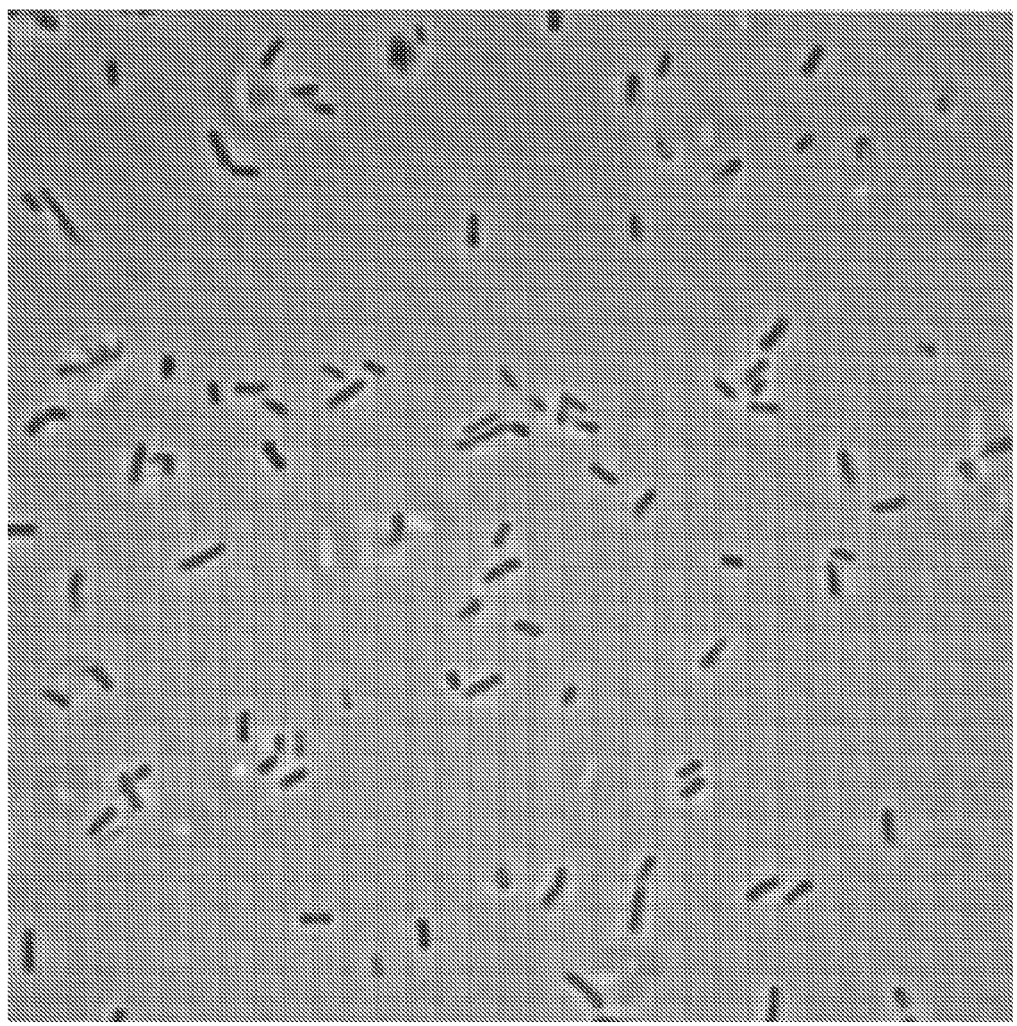
FIG. 3 is the morphology of *Lactobacillus reuteri* GMNL-263 under microscope.

Isolated strain GMNL-263 was subjected to bacteriological scientific name identification in the Food Development and Research Institute, as described briefly hereinafter:

Background Information of Isolated Strain GMNL-263:
1. Sources: gastrointestinal tract of human body
2. Medium: MRS
3. Culturing temperature: 37° C.
4. Pathogenicity: no Referring to FIG. 3 and Table 4, analysis results indicated that isolated strain GMNL-263 Referring to FIG. 1 and Table 2, analysis results indicated that isolated strain GMNL-263 was a Gram-positive bacillus without catalase, oxidase and mobility, and could be grown under both aerobic and anaerobic environments. Further, part 16S rDNA sequence of the isolated strain GMNL-263 is shown as in SEQ ID No: 2. In accordance with this 16S rDNA analysis, isolated strain GMNL-263 is more similar with *Lactobacillus reuteri*, with an identity up to higher than 99%. Moreover, by means of API identification systematic analysis (Table 4), isolated strain GMNL-263 is closest to *Lactobacillus reuteri*. Therefore, according to the above-described results, isolated strain GMNL-263 is *Lactobacillus reuteri*.

TABLE 4

API identification analysis results of isolated strain GMNL-263

| API Test | isolated strain GMNL-263 | *Lactobacillus reuteri* |
|---|---|---|
| Glycerol | − | − |
| Erythritol | − | − |
| D-Arabinose | − | − |
| L-Arabinose | + | + |
| D-Ribose | − | + |
| D-Xylose | − | − |
| L-Xylose | − | − |
| D-Adonitol | − | − |
| Methyl-βD-Xylopyranoside | − | − |
| D-Galactose | + | + |
| D-Glucose | + | + |
| D-Fructose | − | + |
| D-Mannose | − | − |
| L-Sorbose | − | − |
| L-Rhamnose | − | − |
| Dulcitol | − | − |
| Inositol | − | − |
| D-Mannitol | − | − |
| D-Sorbitol | − | − |
| Methyl-αD-mannopyranoside | − | − |
| Methyl-αD-glucopyranoside | − | − |
| N-AcetylGlucosamine | − | − |
| Amygdalin | − | − |
| Arbutin | − | − |

TABLE 4-continued

API identification analysis results of isolated strain GMNL-263

| API Test | isolated strain GMNL-263 | *Lactobacillus reuteri* |
|---|---|---|
| Esculin | − | − |
| Salicin | − | − |
| D-Celiobiose | − | − |
| D-Maltose | + | + |
| D-Lactose | − | + |
| D-Melibiose | + | + |
| D-Saccharose | + | + |
| D-Trehalose | − | − |
| Inulin | − | − |
| D-Melezitose | − | − |
| D-Raffinose | + | + |
| Amidon | − | − |
| Glycogen | − | − |
| Xylitol | − | − |
| Gentiobiose | − | − |
| D-Turanose | − | − |
| D-Lyxose | − | − |
| D-Tagatose | − | − |
| D-Fucose | − | − |
| L-Fucose | − | − |
| D-Arabitol | − | − |
| L-Arabitol | − | − |
| Potassium Gluconate | + | + |
| Potassium 2-Ketogluconate | − | − |
| Potassium 5-Ketogluconate | − | − |
| Number of coincident items between isolated strain GMNL-263 and standard strain: | | 46 |

− Negative reaction;
+ Positive reaction 3-2. Gene Chromatogram Analysis of *Lactobacillus* GMNL-263 Strain Gene chromatogram of *Lactobacillus* GMNL-263 strain was analyzed by means RAPD analysis according to the RAPD experimental procedure as described in Example 2-2 A to B. In which, strains analyzed were *Lactobacillus reuteri* GMNL-263 and *Lactobacillus reuteri* GMNL-89.

Experimental Results

Figure 4:
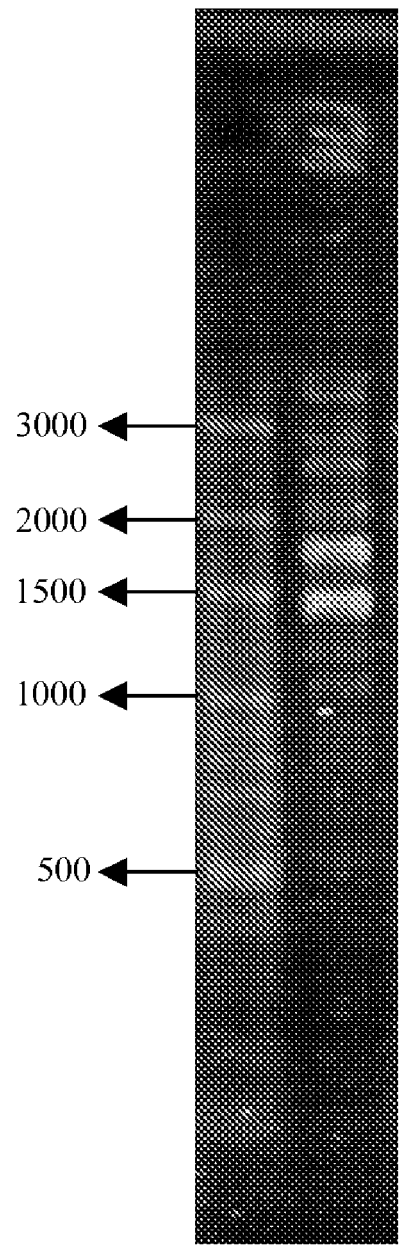
FIG. 4 is the gene chromatogram gene chromatogram of *Lactobacillus reuteri* GMNL-263 and GMNL-89; in which M represents molecular marker; and each arrow indicates molecular size (bp) of each fragment.
Figure 4:
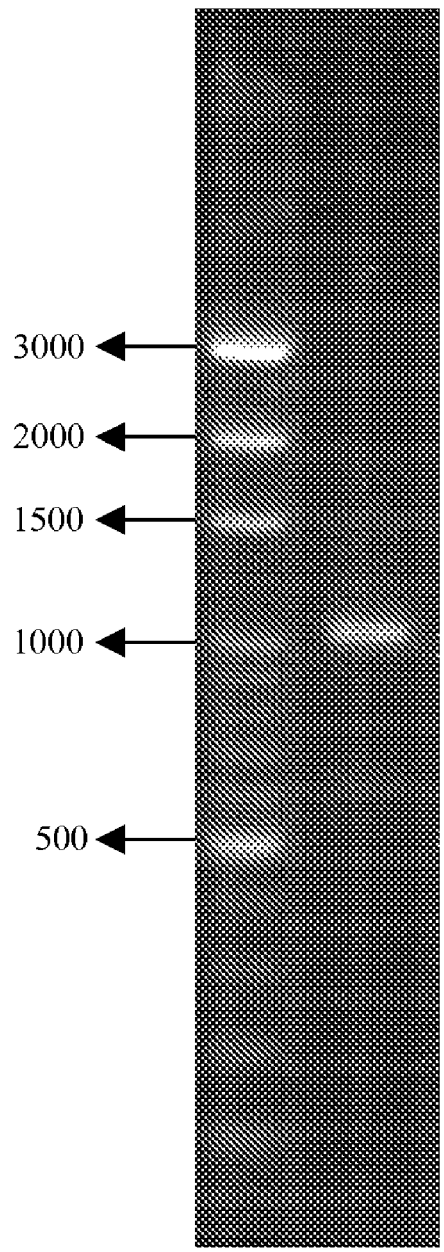
Figure 5A:
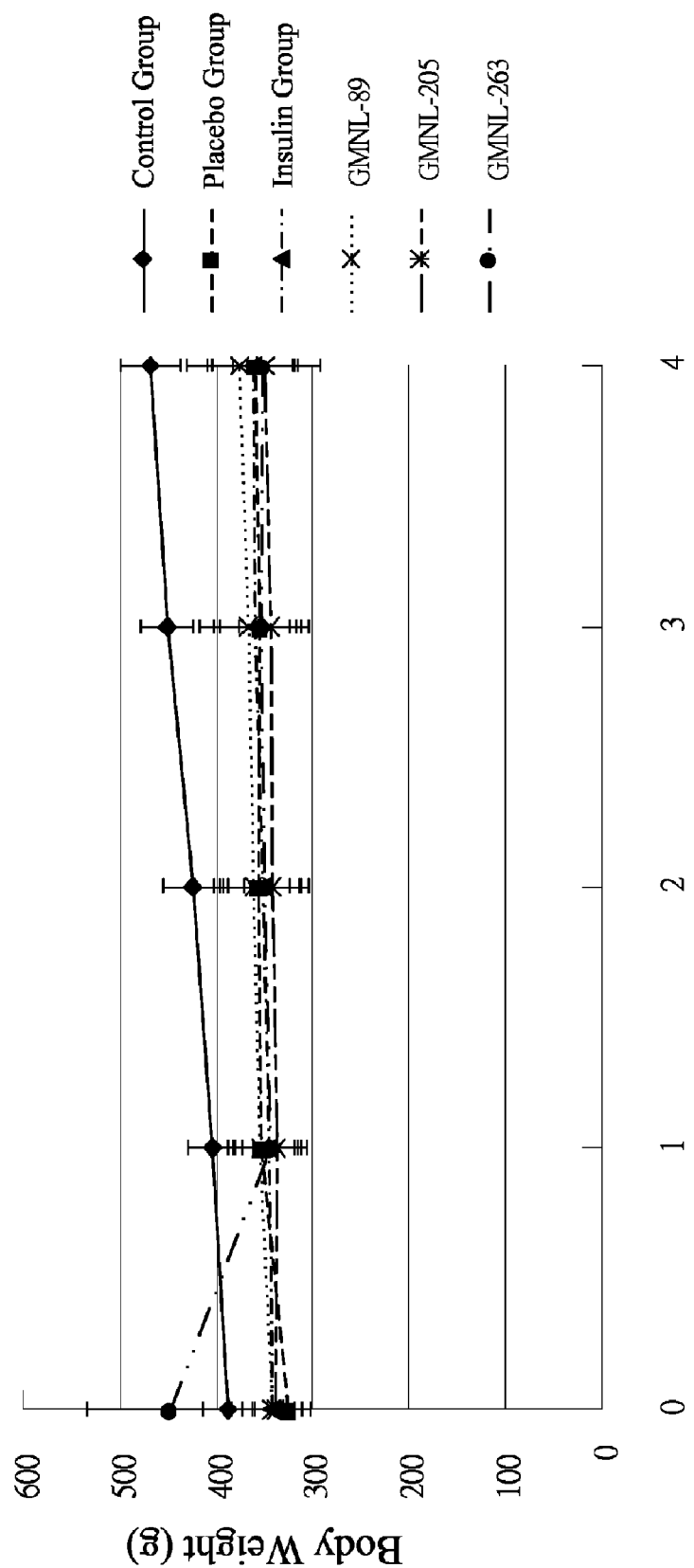
FIG. 5A shows body weight results of diabetes rats in each group recoded weekly.
Figure 5:
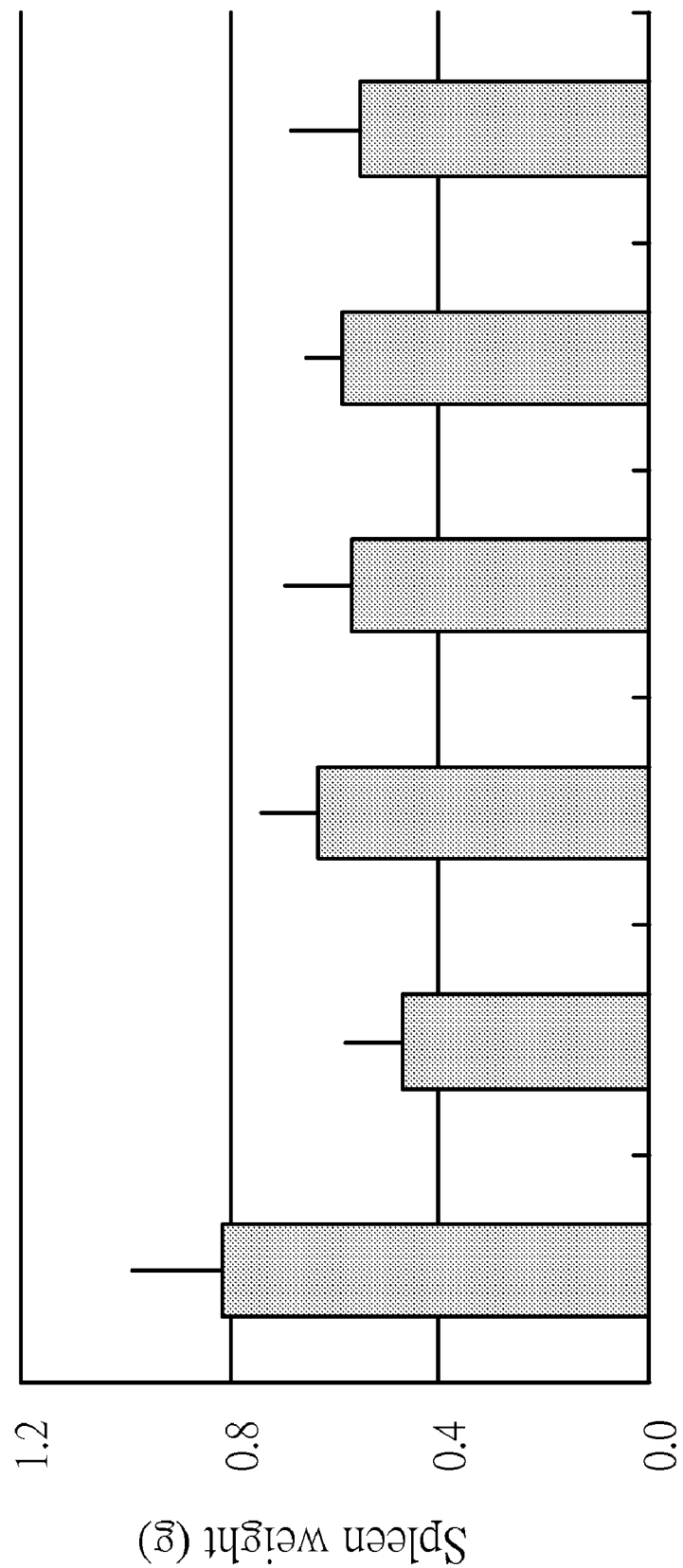
FIG. 5B shows spleen weight results of diabetes rats in each group.
FIG. 5C shows liver weight results of diabetes rats in each group.
FIG. 5D shows kidney weight results of diabetes rats in each group.
Figure 5:
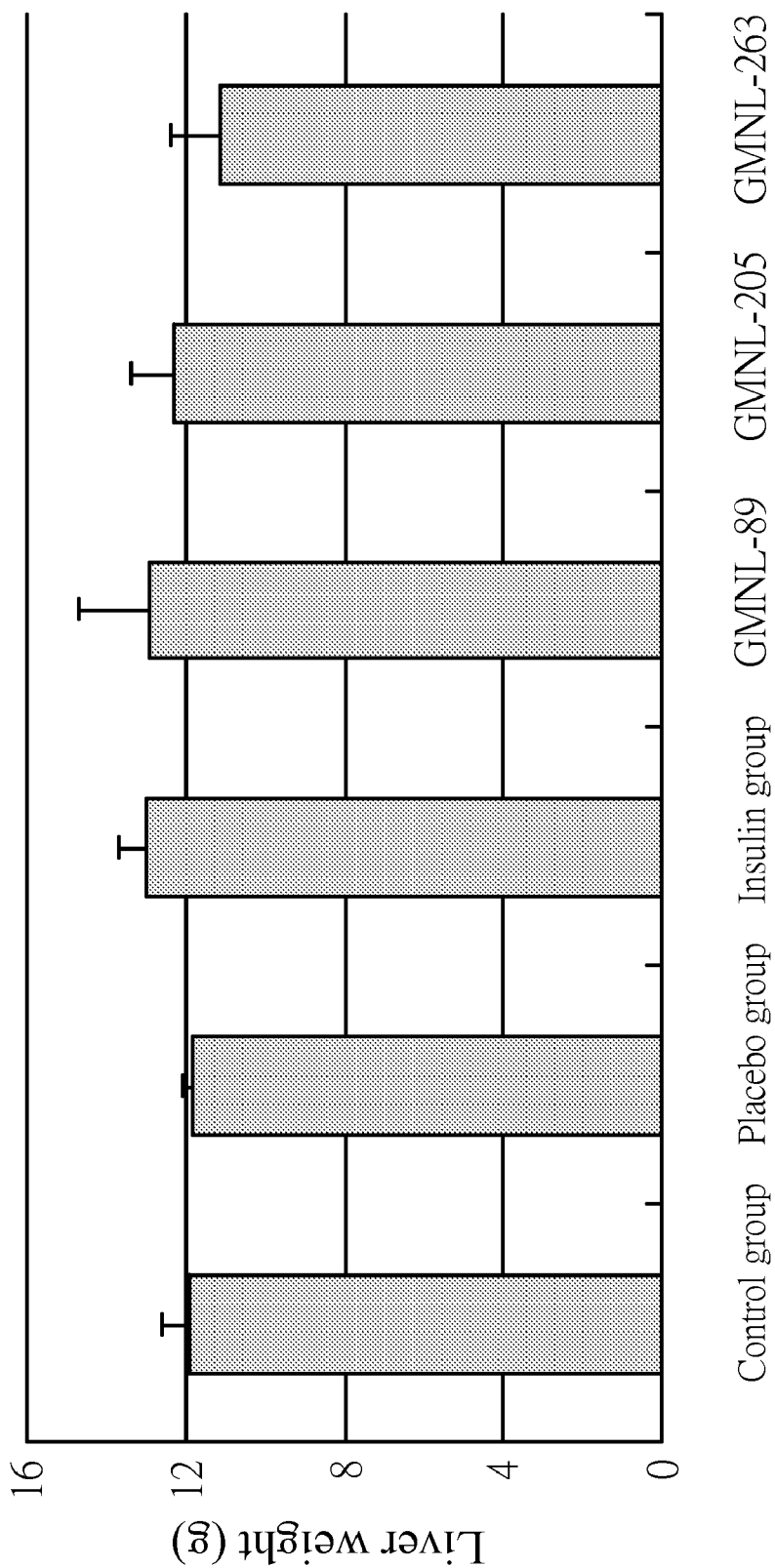
Figure 5:
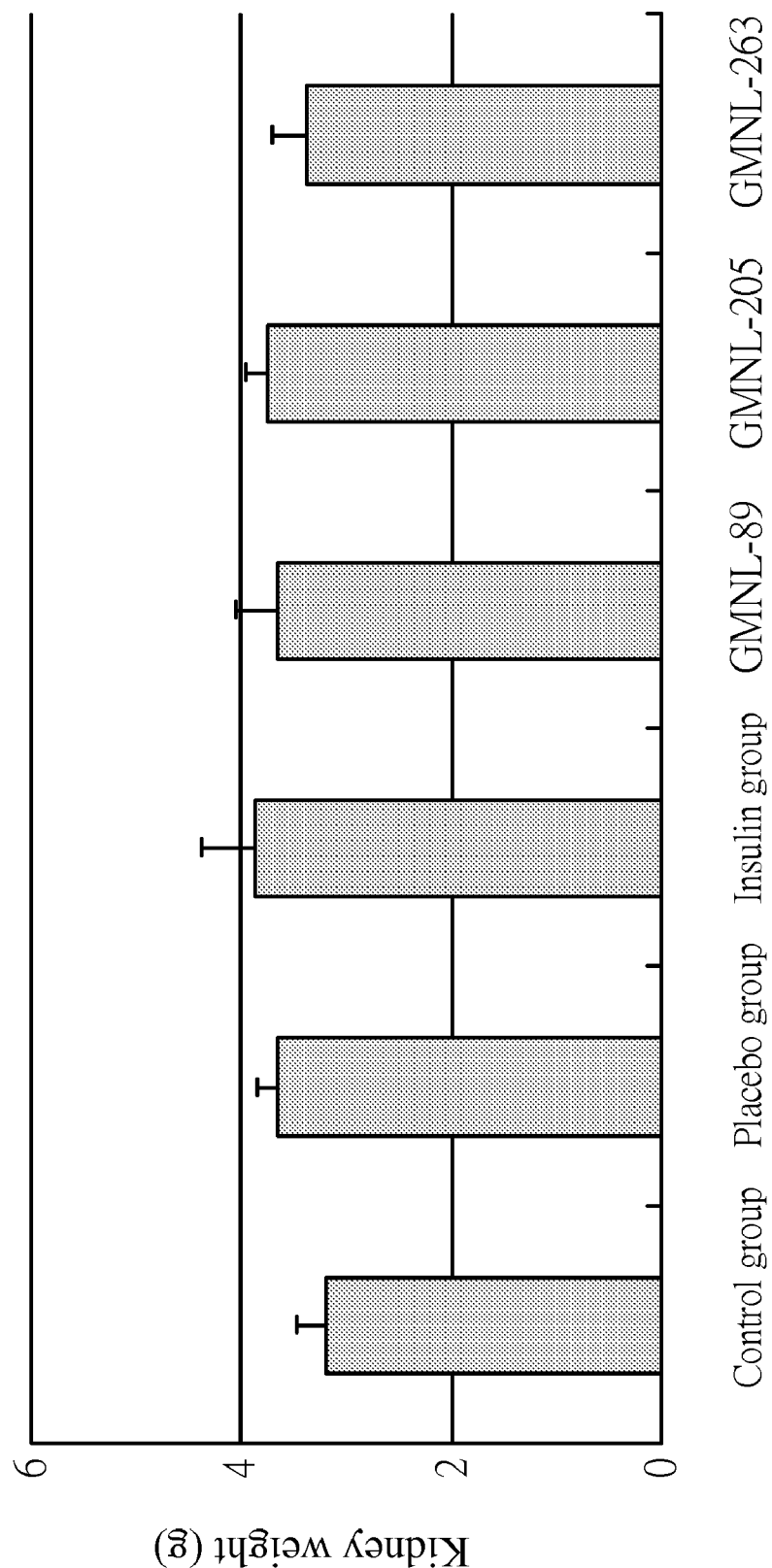

Referring to FIG. 4, very great difference between gene chromatograms of GMNL-89 and GMNL-263 is clearly shown. This indicates that GMNL-89 and GMNL-263 are same *Lactobacillus reuteri*, but not same strain.

EXAMPLE 4

Diabetes Animal Model 4-1. Experimental Animals 5 week-old male SD rats were purchased from BioLASCO Taiwan Co., Ltd. and after being kept in house for accommodating one week, were used in animal experiment. During the whole experiment, rats were kept in animal house under 12 hours each of dark and light period without limiting feeding or drinking. The house was maintained at room temperature of 24±1° C. and relative humidity of 55%. In this study, treatments on animals and all experimental procedure were performed in accordance with standard regulation stipulated by International Committee on Laboratory Animal.

4-2. Induction of Diabetes

Rats were induced into diabetes animal model by means of following method: Dissolving streptozotocin (STZ) in citrate buffer (containing 0.1 M citrate acid and 0.1M sodium citrate, pH 4.5); fasting rats for 24 hours, intraperitoneal injecting 65 mg/kg of STZ solution; after 3 days, determining blood sugar value, the induction was considered as finished if blood sugar higher than 300 mg/dL.

EXAMPLE 5

Evaluation of the Effect of *Lactobacillus* Isolated Strain for Improving Diabetes and Associated Index 5-1. Experimental Protocol Rats were divided randomly into 6 groups according to treating ways as described in Table 5. In the control group, no STZ-induction of diabetes was carried out, while in all of other groups, after STZ-induction of diabetes, rats were fed with reverse osmosis water (RO water), placebo (placebo group), injecting insulin (insulin group), or fed with bacteria of respective *Lactobacillus* isolated strains. One month later, rats were sacrificed and their sera were sampled for determining various biochemical indexes. Results thus obtained were used to evaluate effects of each *Lactobacillus* isolated strain on the improvement of diabetes and associated index.

TABLE 5

Experimental groups

| Group | Treatment |
|---|---|
| Control group | NoIntraperitoneal injecting STZ, feeding 1 ml RO water daily |
| Placebo group | Intraperitoneal injecting STZ, feeding 1 ml RO water daily |
| Insulin group | Intraperitoneal injecting STZ, Intraperitoneal injectingInsulin 7-10 U/Kg daily |
| GMNL-89 group | Intraperitoneal injecting STZ, feeding *Lactobacillus* isolated strain GMNL-89 $2 \times 10^9$ cfu/day daily |
| GMNL-205 group | Intraperitoneal injecting STZ, feeding *Lactobacillus* isolated strain GMNL-205 $2 \times 10^9$ cfu/day daily |
| GMNL-263 group | Intraperitoneal injecting STZ, feeding *Lactobacillus* isolated strain GMNL-263 $2 \times 10^9$ cfu/day daily |

5-2. Determination of Relative Indexes:

Body Weight and Blood Sugar Value

In the course of experiment, blood sugar value was determined every morning and evening, and body weight was determined once every week.

1. Determination of biochemical index in serum

Serum biochemical values: alkaline phosphatase, alanine aminotransferase, aspartate aminotransferase, γ-glutamyl transferase (γ-GP), albumin, total bilirubin, creatinine, urea nitrogen, glucose, phosphorus, calcium, chloride, potassium, sodium, total protein, triglyceride, total cholesterol, HDL, LDL, c-reactive protein (CRP), and Glycated hemoglobin (HbA1c).

Blood differential counting: complete blood counting (CBC).

2. Determination of cytokine: Serum IFN-γ concentration was determined by ELISA assay.

3. Determination of liver lipid:

Rats were sacrificed and right lower biggest liver leaf was removed. 0.25 g liver was weighed and was placed in each of two 1.5 ml microcentrifuge tubes used specifically for tissue homogenizer (Model: MICROMOT IB/E, PROXXON), respectively. To each tube, 0.5 ml extraction solution (chloroform/methanol mixed solution 2:1 v/v), was added and homogenized at 10,000 rpm for about 20 seconds. Homogenized liquor in both microcentrifuge tubes was poured in a 15-ml FALCON centrifuge tube. Both microcentrifuge tubes were washed each with 1 ml chloroform/methanol mixed solution (2:1 v/v) from microdispenser, poured into the above-described 15-ml FALCON centrifuge tube, and finally, 7 ml of chloroform/methanol mixed solution (2:1 v/v) was added (total volume 10 ml). 250 μl of thus-obtained liver lipid extracted solution was mixed well with 250 μl Triton X-100 (Sigma). The mixed solution was subjected to the determination of total cholesterol, and triglyceride in liver.

5-3. Statistical Test

Statistical test used in the invention is student's test.

5-4. Results

A. Body Weight

Referring to FIG. 5A to 5D, compared with the placebo group, body weights of diabetes rats in each *Lactobacillus*-administrating group one month after fed with bacteria of respective *Lactobacillus* isolated strain did not show any significant change. Likewise, weights of liver, spleen and kidney in each *Lactobacillus*-administrating group did not show significant difference with those in the placebo group.

B. Blood Sugar and Other Ions

Figure 6A:
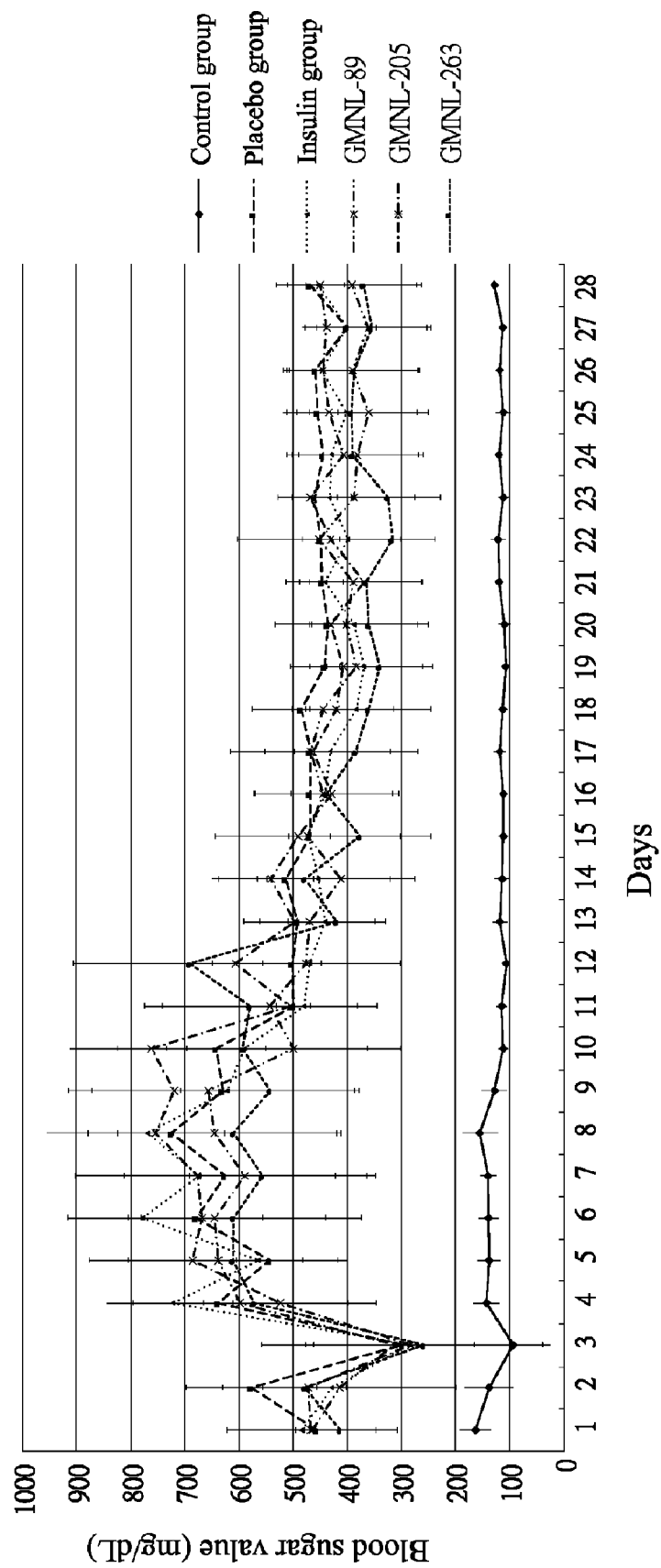
FIG. 6A shows daily blood sugar value results of diabetes rats in each group.
Figure 6:
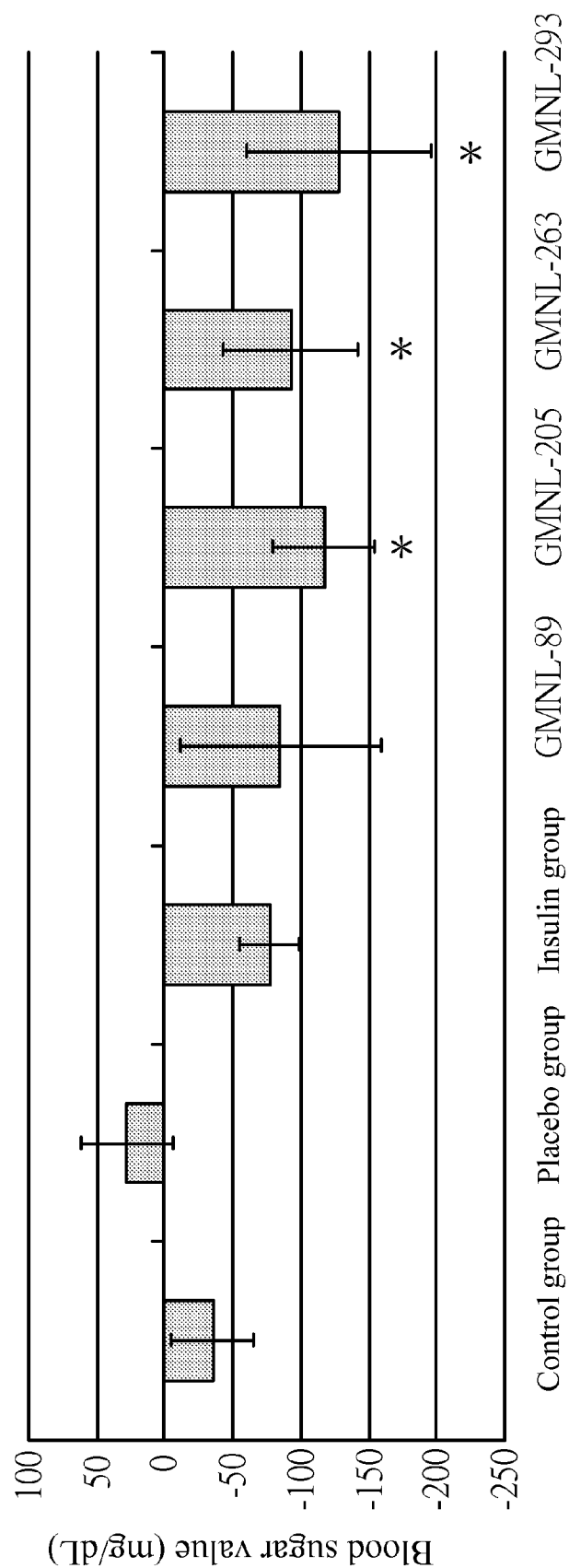
FIG. 6B shows analytical results of blood sugar value change of diabetes rats in each group; * represents statistical significance of the data compared with that of placebo group ($p<0.05$)

Referring to FIGS. 6A and 6B, blood sugar value changes of diabetes rats in isolated strain GMNL-205 or GMNL-263 groups were lowered remarkably compared with that in the placebo group. Therefore, fed with bacteria of *Lactobacillus* isolated strains GMNL-205 or GMNL-263 could lower effectively the high blood sugar value and blood sugar value change of diabetes subjects. In aspect of blood ion concentrations (referring to Table 6), *Lactobacillus*-administrating groups did not show significant difference with those of the placebo group.

TABLE 6

Blood ion concentrations of diabetes rats determined one month after feeding GMNL-89, GMNL-205 and GMNL-263

|  | Normal | Placebo | Insulin |
|---|---|---|---|
| Na (mEq/l) | 147.267 ± 3.823 | 140.733 ± 6.381 | 144.175 ± 1.882 |
| K (mEq/l) | 12.785 ± 1.548 | 8.473 ± 0.363 | 9.53 ± 1.332 |
| Cl (mEq/l) | 88.65 ± 3.849 | 79.4 ± 5.897 | 79.15 ± 3.122 |
| Ca (mg/dl) | 8.933 ± 1.305 | 9.4 ± 0.7 | 8.825 ± 2.027 |
| P (mg/dl) | 26.483 ± 2.27 | 17.833 ± 3.717 | 21.9 ± 2.481 |

|  | GMNL-89 | GMNL-205 | GMNL-263 |
|---|---|---|---|
| Na (mEq/l) | 144.013 ± 2.446 | 140.314 ± 2.021 | 141.171 ± 4.162 |
| K (mEq/l) | 9.298 ± 2.827 | 10.093 ± 2.367 | 9.704 ± 2.023 |
| Cl (mEq/l) | 79.813 ± 4.222 | 80.8 ± 2.918 | 83.114 ± 4.819 |
| Ca (mg/dl) | 10.075 ± 0.933 | 9.343 ± 1.356 | 8.514 ± 1.899 |
| P (mg/dl) | 22.038 ± 4.779 | 18.529 ± 3.528 | 17.857 ± 4.357 |

C. Serum Biochemical Values

Figure 7A:
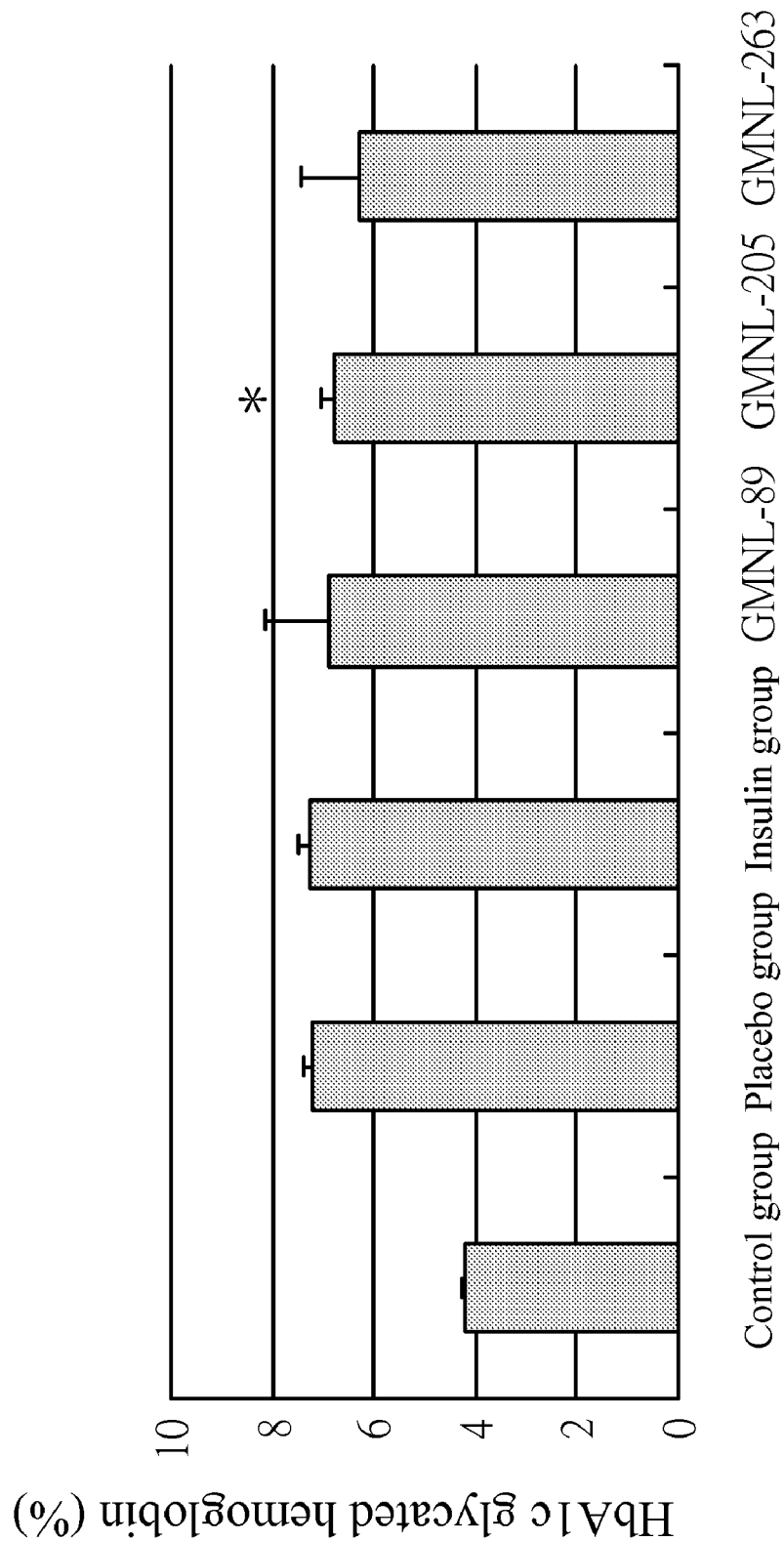
FIG. 7A shows glycated hemoglobin level (HbA1c) of diabetes rats in each group.
Figure 7:
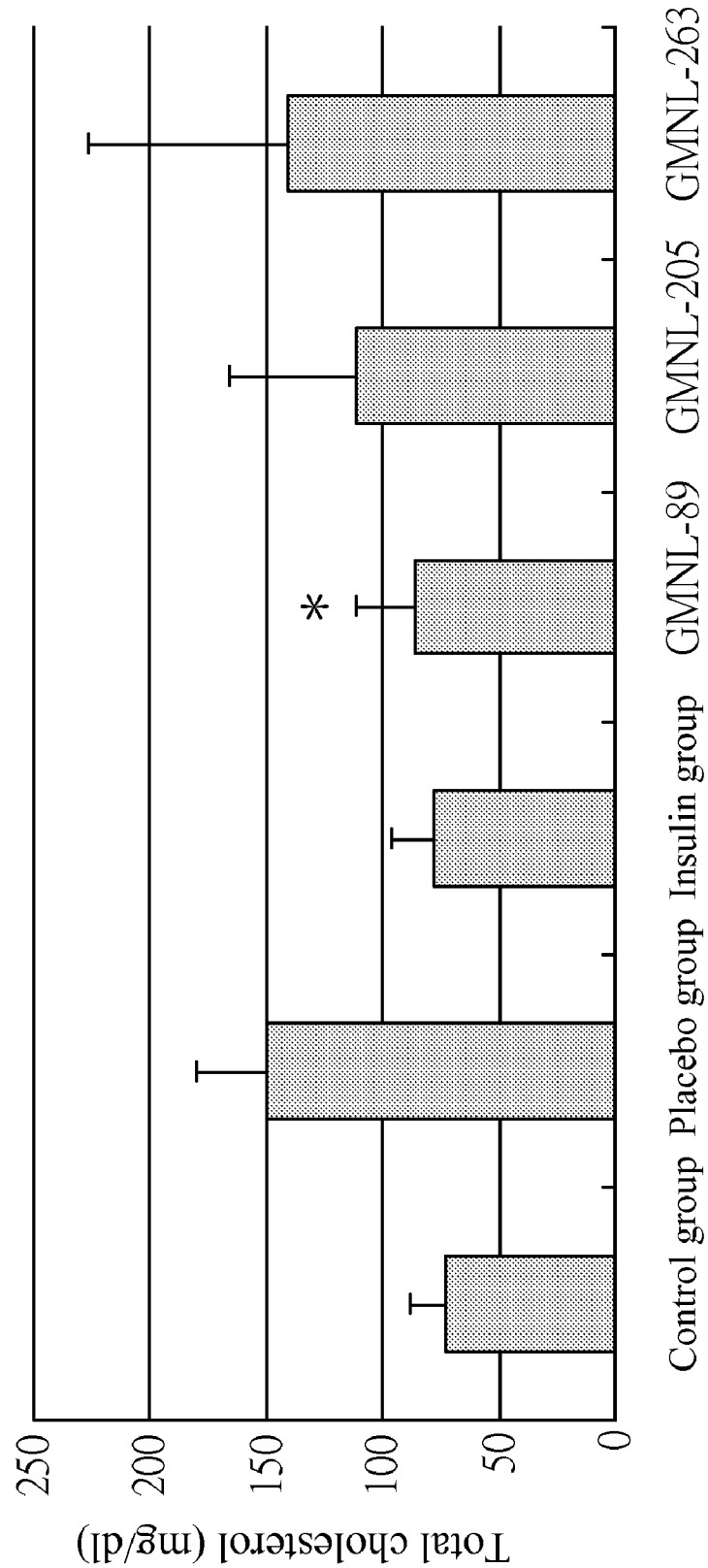
FIG. 7B shows total cholesterol concentration of diabetes rats in each group.
FIG. 7C shows analytical results of LDL/HDL ratio of diabetes rats in each group; * represents statistical significance of the data compared with that of placebo group ($p<0.05$)
Figure 7C:
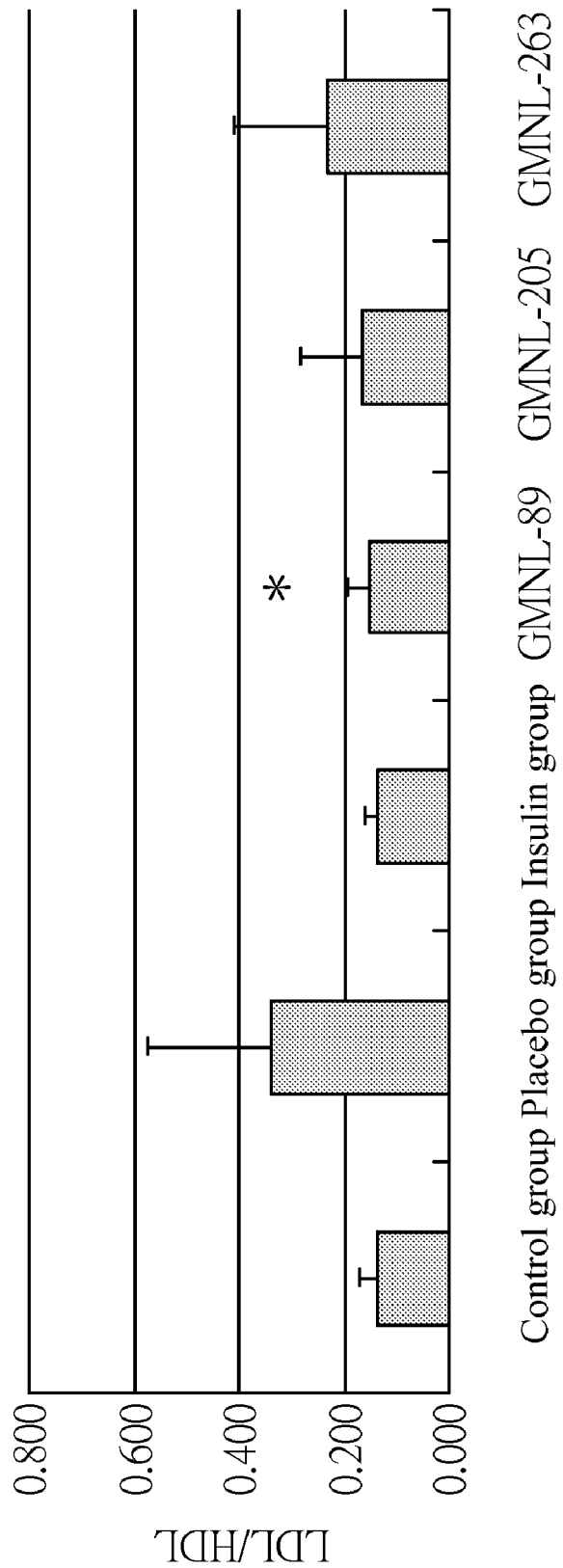

Referring to FIG. 7A to 7C and Table 7, after fed with GMNL-205 for one month, serum glycated hemoglobin (HbA1c) concentration of diabetes rats did lower remarkably compared with that in the placebo group; after fed with GMNL-89 for one month, serum total cholesterol concentration and LDL/HDL ratio in diabetes rats did lower significantly also compared with those in the placebo group, while other groups did not show significant difference. With respect to the improvement of liver function index, after fed with GMNL-89 for one month, serum concentrations of GOT and GPT of diabetes rats tended to be lower compared with those in the placebo group. In addition, after fed with GMNL-263 for one month, serum GPT concentration of diabetes rats tended to be lower also compared with that in the placebo group.

In the life cycle of red blood cell (average about 120 days), hemoglobin will be glycated gradually by sugar in the blood. Therefore, in addition to monitor blood sugar value and value change of diabetes subjects, HbA1C has been used extensively as the index indicating the condition in controlling blood sugar of diabetes subjects. Further, research has pointed out that, other than obviously high blood sugar concentration, diabetes subject also had remarkably increased blood cholesterol concentration, and therefore, risk of cardiovascular disease was increased significantly, too. The above-described results indicated that, after fed with *Lactobacillus* isolated strain GMNL-205 for one month, glycated hemoglobin value of diabetes subjects could be lowered effectively. This reflected that, long-term administration of said *Lactobacillus* isolated strain GMNL-205 could control blood sugar value change in the body of diabetes subjects. Furthermore, after fed with *Lactobacillus* isolated strain GMNL-89 for one month, total cholesterol concentration and LDL/HDL ratio of diabetes subjects could be lowered effectively, and hence decrease further the risk of cardiovascular disease or diseases or complication associated with excess high cholesterol for diabetes subjects.

Further, with respect to blood differential counting (Table 8), all *Lactobacillus* groups did not show significant difference with that in the placebo group.

D. Cytokine

Figure 8:
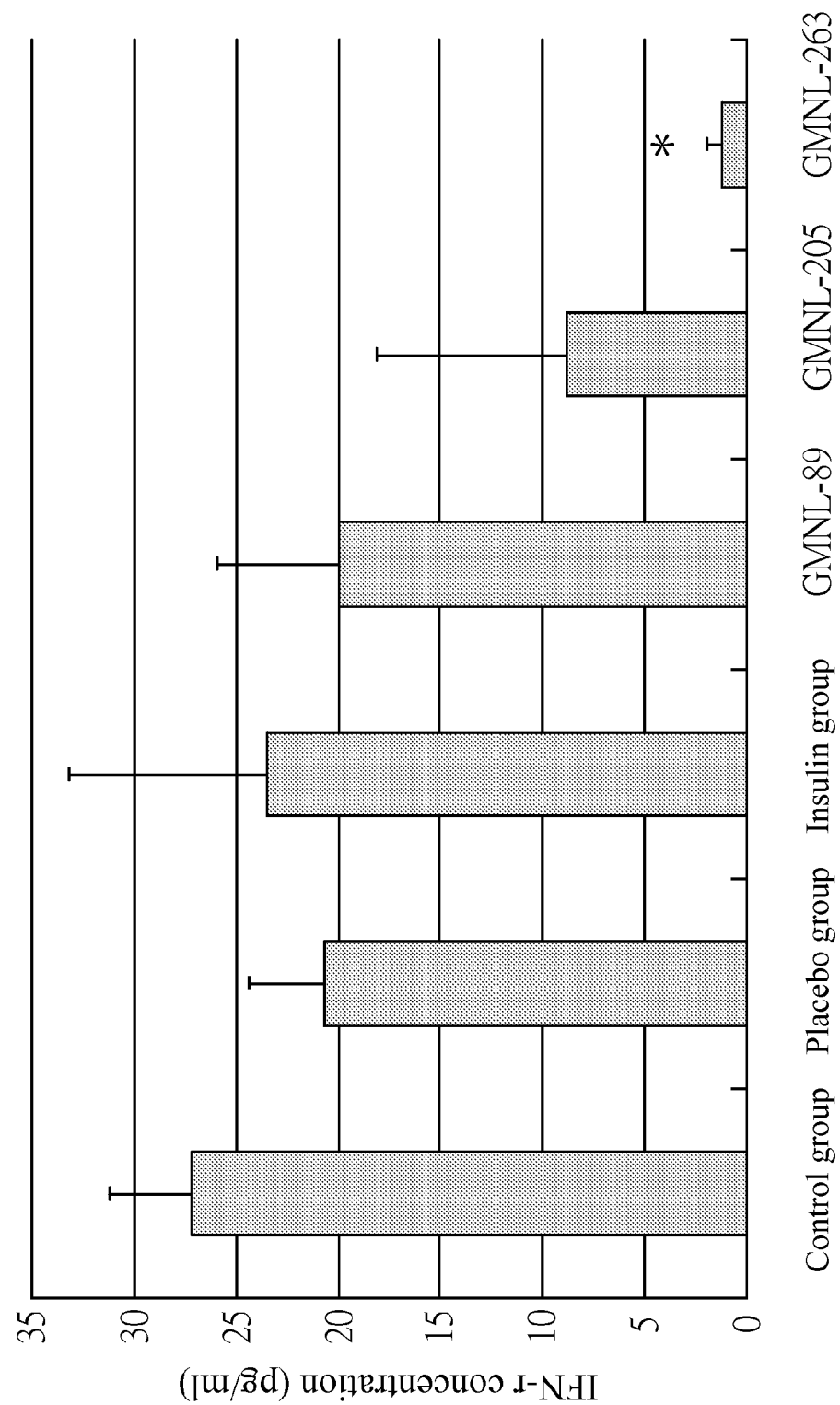
FIG. 8 shows cytokine IFN-γ concentration in serum of diabetes rats in each group; * represents statistical significance of the data compared with that of placebo group ($p<0.05$)

Referring to FIG. 8, after fed with *Lactobacillus* isolated strain GMNL-263 for one month, serum IFN-γ concentration of diabetes rats in *Lactobacillus*-administrating groups were lowered significantly compared with that in the placebo group. In recent years, many literatures have pointed out that diabetes had been linked closely with inflammation reaction, which would lead often to the complication of chronic inflammation in diabetes subjects. In this experiment, it was demonstrated that, after fed with *Lactobacillus* isolated strain GMNL-263 for one month, in addition to improving effectively the blood sugar value of diabetes subjects, inflammation-associated cytokine IFN-γ concentration in serum of diabetes subjects could be lowered effectively also, which indicated that fed with said *Lactobacillus* isolated strains could improve effectively diabetic inflammation reaction or associated complication.

E. Liver Lipid

Figure 9A:
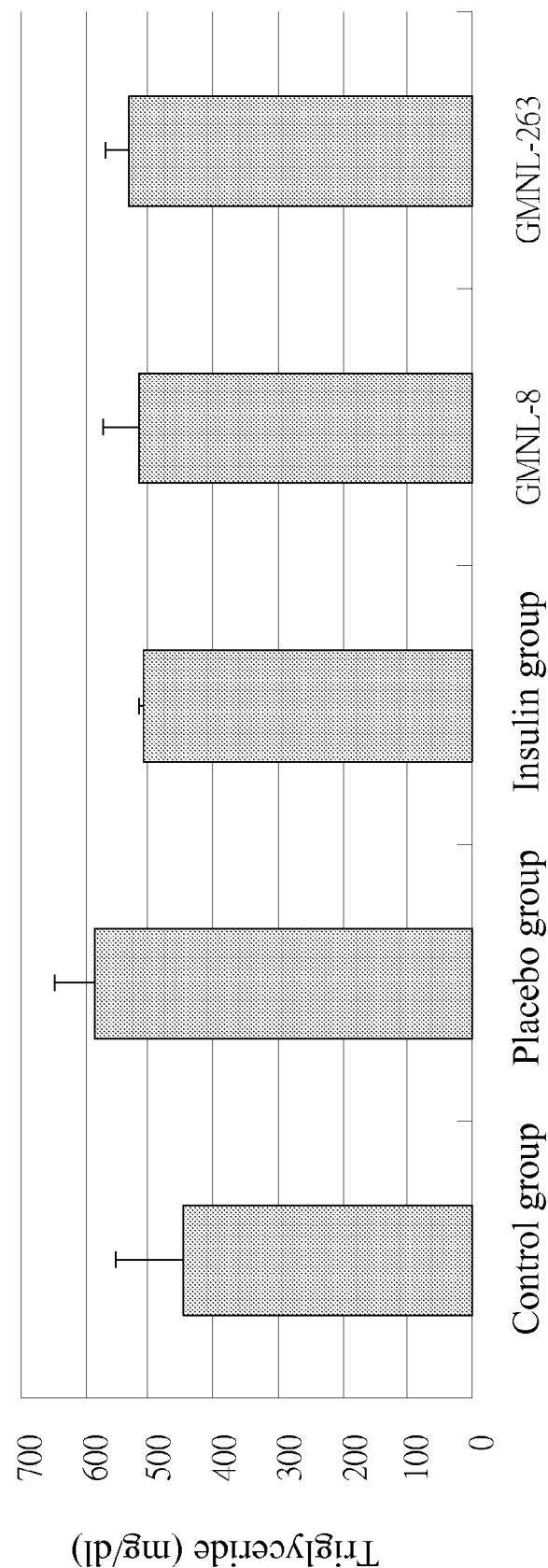
FIG. 9A shows determination results of liver triglyceride level of diabetes rats in each group.
Figure 9:
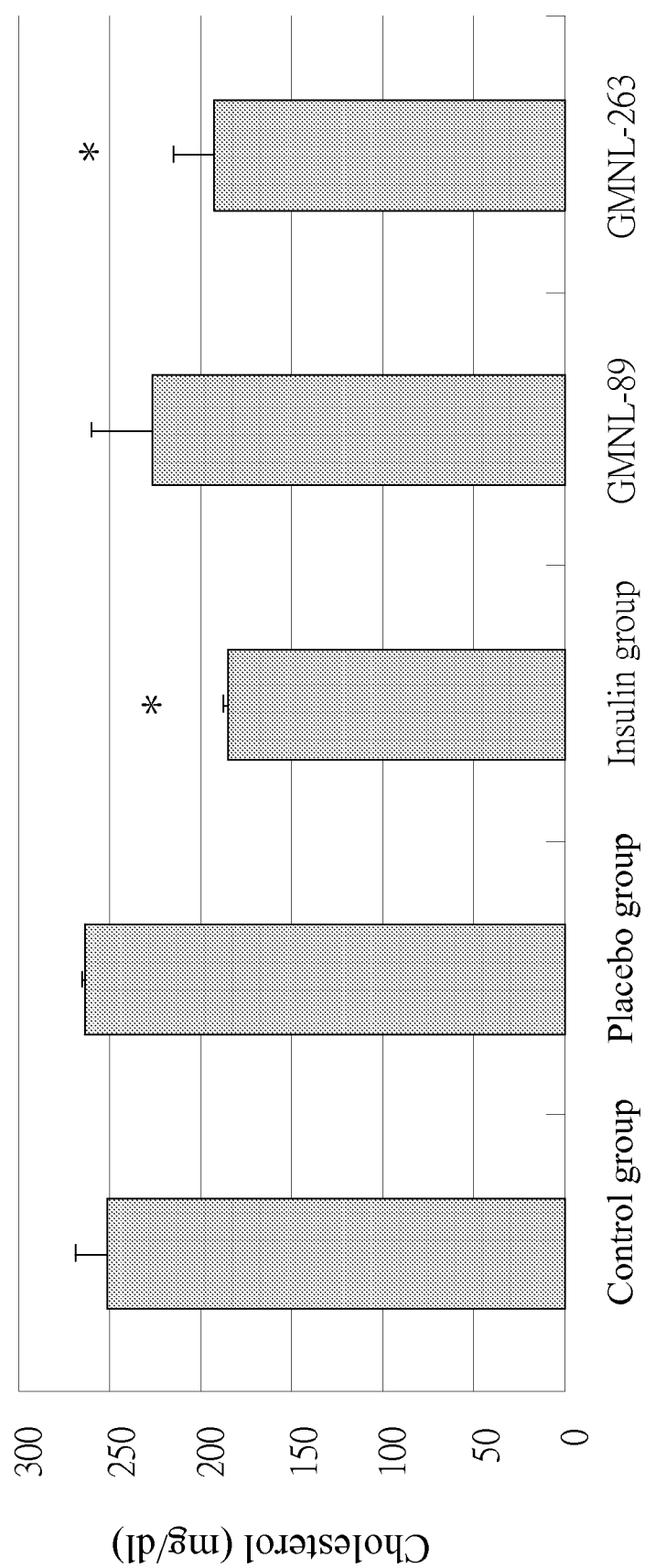
FIG. 9B shows determination results of liver cholesterol level of diabetes rats in each group; * represents statistical significance of the data compared with that of placebo group ($p<0.05$).

Referring to FIG. 9A, liver triglyceride concentration of diabetes rats in groups fed with *Lactobacillus* isolated strains GMNL-89 or GMNL-263 tended to decrease compared with that in the control group. Referring to FIG. 9B, liver cholesterol concentration of rats fed with *Lactobacillus* isolated strain GMNL-89 tended to decrease compared with that in the control group; while liver cholesterol concentration of rats fed with *Lactobacillus* isolated strain GMNL-263 did decrease significantly compared with that in the control group.

These results indicate that, diabetes subjects administrated with the inventive *Lactobacillus*, compared with those not administrated with these bacteria, could lower effectively liver triglyceride and cholesterol concentrations, and reduce further the risk of non-alcoholic fatty liver.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

TABLE 7

Serum biochemical results of diabetes rats determined one month after feeding GMNL-89, GMNL-205, or GMNL-263

| | Control group | Placebo group | Insulin group | GMNL-89 | GMNL-205 | GMNL-263 |
|---|---|---|---|---|---|---|
| HbA1c (%) | 4.2 ± 0.089 | 7.2 ± 0.173 | 7.25 ± 0.238 | 6.913 ± 1.203 | 6.8 ± 0.245* | 6.286 ± 1.173 |
| Total protein (g/dl) | 6.7 ± 0.424 | 5.333 ± 0.289 | 5.875 ± 0.287 | 5.95 ± 0.548 | 5.257 ± 0.346 | 5.457 ± 0.562 |
| Albumin (g/dl) | 4.367 ± 0.288 | 3.6 ± 0.265 | 3.425 ± 0.126 | 3.838 ± 0.283 | 3.543 ± 0.299 | 3.6 ± 0.4 |
| A/G Ratio | 1.883 ± 0.147 | 2.067 ± 0.153 | 1.425 ± 0.126* | 1.888 ± 0.348 | 1.929 ± 0.243 | 1.986 ± 0.344 |
| GOT (units) | 277.5 ± 52.687 | 546.333 ± 81.929 | 407 ± 86.76 | 418.875 ± 246.526 | 609.857 ± 225.069 | 554 ± 307.77 |
| GPT (units) | 48.333 ± 7.23 | 235 ± 26.211 | 100.25 ± 40.352* | 159.25 ± 113.235 | 239.571 ± 105.065 | 199 ± 124.988 |
| Total Bilirubin (mg/dl) | 0.15 ± 0.055 | 0.333 ± 0.231 | 0.225 ± 0.096 | 0.3 ± 0.177 | 0.343 ± 0.172 | 0.371 ± 0.189 |
| γ-GT (IU/l) | 0.1 ± 0 | 9.767 ± 4.186 | 2.15 ± 2.456* | 6.4 ± 4.444 | 8.9 ± 5.725 | 9.5 ± 11.684 |
| CRP (mg/dl) | 0.01 ± 0 | 0.053 ± 0.04 | 0.01 ± 0 | 0.185 ± 0.211 | 0.159 ± 0.241 | 0.051 ± 0.105 |
| BUN (mg/dl) | 29.017 ± 2.073 | 44.4 ± 9.358 | 44.025 ± 7.258 | 42.825 ± 6.804 | 44.429 ± 6.748 | 45.2 ± 12.466 |
| Creatinine (mg/dl) | 0.617 ± 0.041 | 0.433 ± 0.058 | 0.525 ± 0.05 | 0.513 ± 0.083 | 0.414 ± 0.09 | 0.429 ± 0.111 |
| Triglyceride (mg/dl0 | 59.167 ± 11.907 | 393.333 ± 81.402 | 201.75 ± 41.732* | 269.75 ± 233.066 | 519.143 ± 395.062 | 387.571 ± 318.053 |
| total Cholesterol (mg/dl) | 73.333 ± 14.459 | 150 ± 30.199 | 78 ± 18.493* | 85.75 ± 25.789* | 111.714 ± 54.227 | 140.571 ± 85.893 |
| LDL/HDL | 0.136 ± 0.032 | 0.341 ± 0.233 | 0.138 ± 0.023 | 0.149 ± 0.046* | 0.163 ± 0.119 | 0.231 ± 0.177 |

*$p < 0.05$, data has statistical significance compared with that of placebo group

TABLE 8

Blood differential counting values of diabetes rats one month after feeding GMNL-89, GMNL-205 or GMNL-263,

| | Control group | Placebo group | Insulin group | GMNL-89 | GMNL-205 | GMNL-263 |
|---|---|---|---|---|---|---|
| WBC (1000/μl) | 9.42 ± 2.94 | 5.23 ± 1.62 | 10.33 ± 2.88* | 7.91 ± 2.71 | 8.36 ± 3.33 | 7.57 ± 2.52 |
| RBC (10^7/μl) | 7.57 ± 0.86 | 7.57 ± 0.15 | 7.69 ± 0.14 | 8.03 ± 0.57 | 7.829 ± 0.76 | 7.62 ± 1.09 |
| HGB (g/dl) | 14.33 ± 1.37 | 14.233 ± 0.40 | 14.55 ± 0.44 | 14.78 ± 1.52 | 14.47 ± 1.33 | 14.2 ± 1.97 |
| HCT (%) | 46.82 ± 9.30 | 44.77 ± 0.76 | 46.58 ± 0.86* | 47.6 ± 4.74 | 47.21 ± 4.34 | 45.61 ± 6.18 |
| MCV (fl) | 61.55 ± 6.941 | 59.1 ± 1.1 | 60.58 ± 1.19 | 59.15 ± 2.09 | 60.36 ± 1.22 | 59.99 ± 2.81 |
| MCH (pg) | 18.983 ± 0.93 | 18.8 ± 0.361 | 18.925 ± 0.591 | 18.35 ± 0.838 | 18.5 ± 0.497 | 18.657 ± 0.69 |
| PLT (1000/μl) | 623.33 ± 308.21 | 527.67 ± 161.85 | 787.5 ± 78.37* | 595.88 ± 136.14 | 610.57 ± 170.68 | 575 ± 192.28 |
| Lymph % | 75.95 ± 9.03 | 59.5 ± 0.85 | 71.45 ± 8.48 | 65.83 ± 11.28 | 69.014 ± 10.262 | 77.33 ± 12.46 |

*$p < 0.05$, data has statistical significance compared with that of placebo group

What is claimed is:

1. A composition for improving syndrome of diabetes and complication thereof, comprising an effective amount of *Lactobacillus* which is at least one selected from the group consisting of *Lactobacillus reuteri* GMNL-89, *Lactobacillus gasseri* GMNL-205, and *Lactobacillus reuteri* GMNL-263, and a pharmaceutically acceptable vehicle, wherein the deposition number of said *Lactobacillus reuteri* GMNL-89 is CCTCC M207154; the deposition number of said *Lactobacillus gasseri* GMNL-205 is CCTCC M209262; and the deposition number of said *Lactobacillus reuteri* GMNL-263 is CCTCC M209263.

2. A composition as recited in claim 1, comprising further at least one probiotics selected from the group consisting of *Lactobacillus* sp., *Bifidobacterium* sp., *Streptococcus* sp., and yeasts.

3. A composition as recited in claim 1, comprising further at least one edible material selected from the group consisting of water, fluid milk products, milk, concentrated milk, fermented milk, yogurt, sour milk, frozen yogurt, lactic acid bacteria-fermented beverages, milk powder, ice cream, cream cheeses, dry cheeses, soybean milk, fermented soybean milk, vegetable-fruit juices, juices, sports drinks, confectionery, jelly, candies, infant formulas, health foods, animal feeds, Chinese herbals, and dietary supplements.

4. A method for improving syndrome of diabetes and complications thereof, comprising of administering an effective amount of composition as recited in claim 1 to a subject of diabetes for improving and lowering high blood sugar value, the change of blood sugar value, glycated hemoglobin ratio, total cholesterol concentration, LDL/HDL ratio, IFN-$\gamma$ level, liver triglyceride lipid concentration, liver cholesterol concentration and improving liver function index GOT, and GPT, and further improving diabetes and associated complication thereof.

5. A novel *Lactobacillus* isolated strain, which is a deposited strain selected from the following:
   1. *Lactobacillus gasseri* GMNL-205, which is deposited CCTCC (China Center for Type Culture Collection), with deposition number of CCTCC M209262; and
   2. *Lactobacillus reuteri* GMNL-263, which is deposited CCTCC (China Center for Type Culture Collection), with deposition number of CCTCC M209263.

* * * * *